US009927350B2

(12) United States Patent
Schmidt

(10) Patent No.: US 9,927,350 B2
(45) Date of Patent: Mar. 27, 2018

(54) THERMAL PROPERTY MICROSCOPY WITH FREQUENCY DOMAIN THERMOREFLECTANCE AND USES THEREOF

(71) Applicant: TRUSTEES OF BOSTON UNIVERSITY, Boston, MA (US)

(72) Inventor: Aaron J. Schmidt, Cambridge, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 694 days.

(21) Appl. No.: 14/511,903

(22) Filed: Oct. 10, 2014

(65) Prior Publication Data

US 2015/0110150 A1    Apr. 23, 2015

Related U.S. Application Data

(60) Provisional application No. 61/892,099, filed on Oct. 17, 2013.

(51) Int. Cl.
    G01J 5/00      (2006.01)
    G01N 25/20     (2006.01)
    G01N 21/17     (2006.01)
    G01N 21/55     (2014.01)

(52) U.S. Cl.
    CPC ......... *G01N 21/1717* (2013.01); *G01N 21/55* (2013.01); *G01N 2021/1731* (2013.01)

(58) Field of Classification Search
    USPC .................. 374/121, 124, 43, 44
    See application file for complete search history.

(56) References Cited

U.S. PATENT DOCUMENTS

| 4,634,290 A | * | 1/1987 | Rosencwaig | G01N 21/55 |
|---|---|---|---|---|
| | | | | 356/432 |
| 5,377,006 A | * | 12/1994 | Nakata | G01N 21/171 |
| | | | | 356/486 |
| 5,479,259 A | * | 12/1995 | Nakata | G01K 5/52 |
| | | | | 356/432 |
| 5,835,199 A | * | 11/1998 | Phillips | G01S 7/4802 |
| | | | | 356/28.5 |

(Continued)

OTHER PUBLICATIONS

Cahill et al., J. Heat Transfer 124(2):223-241 (2002). "Thermometry and Thermal Transport in Micro/Nanoscale Solid-State Devices and Structures."

(Continued)

*Primary Examiner* — Mirellys Jagan
(74) *Attorney, Agent, or Firm* — Nixon Peabody LLP; Mark J. FitzGerald

(57) ABSTRACT

The present invention relates to frequency domain thermoreflectance (FDTR) imaging of a thermophysical property or a set of thermophysical properties of a sample. A method comprises measuring the amplitude and/or phase of a beam of radiation reflected from a sample surface, while a heat source applied to the sample is modulated at at least two modulation frequencies simultaneously. Such measurement can be reiterated as a probe beam is scanned across the sample surface or a portion thereof. A 2D image or map of a thermophysical property or a set of thermophysical properties can be generated from data processing. Also provided herein is an apparatus for performing FDTR imaging.

20 Claims, 27 Drawing Sheets

(56) References Cited

U.S. PATENT DOCUMENTS

| | | | | |
|---|---|---|---|---|
| 6,168,311 | B1* | 1/2001 | Xiao | G01J 5/58 250/227.11 |
| 9,651,610 | B2* | 5/2017 | Eiles | G01R 31/2656 |
| 2001/0028460 | A1* | 10/2001 | Maris | G01N 21/1702 356/432 |
| 2006/0012791 | A1* | 1/2006 | Reinhorn | G01N 21/9501 356/432 |
| 2006/0055939 | A1* | 3/2006 | Akiba | G01B 11/2441 356/497 |
| 2006/0082781 | A1* | 4/2006 | Chan | G01B 11/2441 356/495 |
| 2008/0036998 | A1* | 2/2008 | Salnik | G01N 21/1717 356/36 |
| 2008/0082288 | A1* | 4/2008 | Raad | G01K 11/125 702/130 |
| 2009/0084959 | A1* | 4/2009 | Hudgings | G01J 5/0003 250/341.8 |
| 2011/0038392 | A1* | 2/2011 | Ando | G01N 25/04 374/16 |
| 2014/0240710 | A1* | 8/2014 | Shigekawa | G01N 21/1717 356/445 |
| 2015/0316496 | A1* | 11/2015 | Chang | H01L 22/12 374/5 |

OTHER PUBLICATIONS

Cahill et al., J. Appl. Phys. 93:793 (2003). "Nanoscale thermal transport."

Cahill et al., Rev. Sci. Instrum. 75:5119 (2004). "Analysis of heat flow in layered structures for time-domain thermoreflectance."

Capinski et al., Phys. Rev. B 59:8105 (1999). "Thermal-conductivity measurements of GaAs/AlAs superlattices using a picosecond optical pump-and-probe technique."

Hopkins et al., J. Heat Transfer 132(8):081302 (2010). "Criteria for Cross-Plane Dominated Thermal Transport in Multilayer Thin Film Systems During Modulated Laser Heating."

Li et al., Journal of the European Ceramic Society, 19(8):1631-1639 (1999). "Measuring the anisotropic thermal diffusivity of silicon nitride grains by thermoreflectance microscopy."

Liu et al., Rev. Sci. Instrum. 84, 034902 (2013). "Simultaneous measurement of thermal conductivity and heat capacity of bulk and thin film materials using frequency-dependent transient thermoreflectance method."

Lopez-Honorato et al., 378(1):35-39 (2008). "Thermal conductivity mapping of pyrolytic carbon and silicon carbide coatings on simulated fuel particles by time-domain thermoreflectance."

Malen et al., J. Heat Transfer 133(8):081601 (2011). "Optical Measurement of Thermal Conductivity Using Fiber Aligned Frequency Domain Thermoreflectance."

Paddock et al., Appl. Phys. 60:285 (1986). "Transient thermoreflectance from thin metal films."

Schmidt et al., J. Appl. Phys. 107, 104907 (2010). "Thermal conductance and phonon transmissivity of metal-graphite interfaces."

Huxtable et al., Nature Mater., 3:298-301 (2004). "Thermal conductivity imaging at micrometre-scale resolution for combinatorial studies of materials."

Schmidt et al., Review of Scientific Instruments, 80:094901 (2009). "A frequency-domain thermoreflectance method for the characterization of thermal properties."

Wei et al., Review of Scientific Instruments, 84:071301 (2013). "Invited Article: Micro resolution spatially resolved measurement of heat capacity using dual frequency time domain thermoreflectance."

Zhu et al., Journal of Appl. Phys., 108:094315-1, (2010). "Ultrafast thermoreflectance techniques for measuring thermal conductivity and interface thermal conductance of thin films."

* cited by examiner

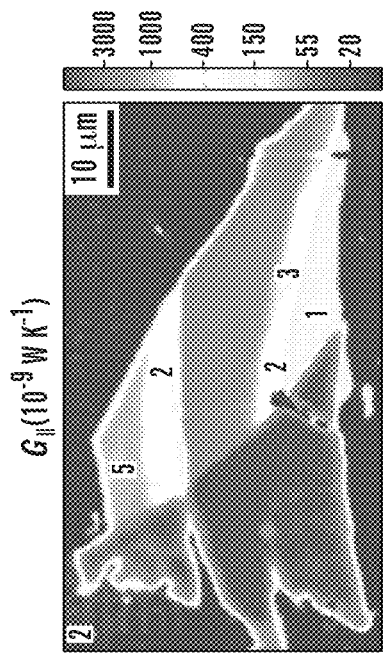
*FIG. 20E*
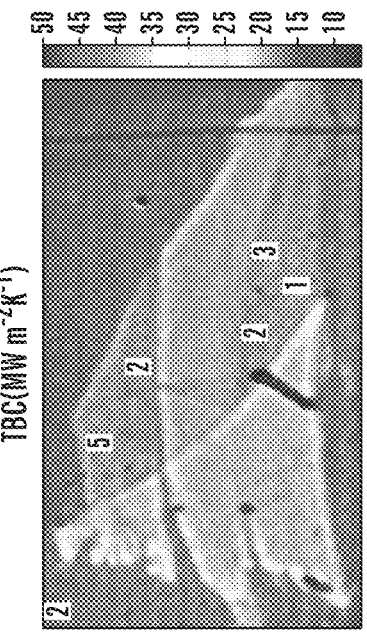
*FIG. 20F*
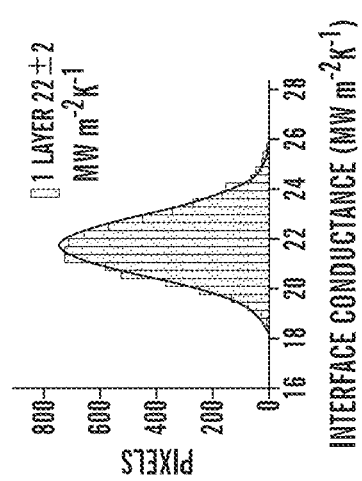
*FIG. 20D*
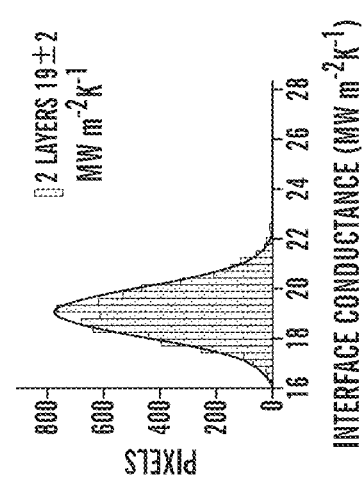

THERMAL PROPERTY MICROSCOPY WITH FREQUENCY DOMAIN THERMOREFLECTANCE AND USES THEREOF

CROSS-REFERENCE TO RELATED APPLICATION

This application claims benefit under 35 U.S.C. § 119(e) of U.S. Provisional Application No. 61/892,099 filed Oct. 17, 2013, the contents of which are incorporated herein by reference in its entirety.

TECHNICAL FIELD

The present invention relates generally to thermoreflectance measurements and imaging of thermal properties.

BACKGROUND

Thermal management plays a critical role in the functionality and reliability of modern microelectronics. As the feature sizes of these devices continue to shrink, researchers have focused on understanding fundamental aspects of thermal transport at the nanoscale, and a variety of experimental techniques have been developed for this purpose (D. G. Cahill, et al., J. Appl. Phys. 93, 793 (2003); D. G. Cahill, et al., J. Heat Transfer 124, 223 (2002)). These include Scanning Thermal Microscopy (SThM), which is based on a heated atomic force microscope tip (O. Kwon, L. Shi, and A. Majumdar, ASME Trans. J. Heat Transfer 125, 156 (2003)), techniques using microfabricated thin film heaters such as the 3ω method (D. G. Cahill, Rev. Sci. Instrum. 61, 802 (1990)), and optical pump-probe methods such as Time-Domain Thermoreflectance (TDTR) (C. A. Paddock and G. L. Eesley, J. Appl. Phys. 60, 285 (1986); W. S. Capinski, et al., Phys. Rev. B 59, 8105 (1999); D. G. Cahill, Rev. Sci. Instrum. 75, 5119 (2004)) and Frequency-Domain Thermoreflectance (FDTR) (A. J. Schmidt, et al., Rev. Sci. Instrum. 80, 094901 (2009); J. Zhu, et al., J. Appl. Phys. 108, 094315 (2010); J. A. Malen, et al., J. Heat Transfer 133, 081601 (2011)). Each of these techniques has relative strengths and weaknesses for quantifying thermal properties in sub-micrometer thin films and across material interfaces. The $3f$ method is a reliable way to measure cross-plane thermal conductivity of materials, but it requires microfabrication, electrical contacts, and its spatial resolution is limited by the dimension of the strip heater deposited above the sample, while SThM provides imaging of thermal properties with nanometer-scale spatial resolution but is extremely sensitive to both sample and tip morphology and requires challenging probe fabrication and complex heat transfer modeling in order to obtain reliable results. TDTR and FDTR are noncontact optical pump-probe techniques, in which one beam of light (the pump) acts as a heat source while a second beam (the probe) detects the resulting temperature change through a change in surface reflectivity. Due to their accuracy and flexibility, they have become increasingly popular methods for determining the thermal properties of thin films.

In TDTR, there is a variable optical delay between the pump and probe pulses from an ultrafast pulsed laser source, while in FDTR the frequency of the modulated pump beam is varied. Both methods typically require the sample to be coated with a thin (~100 nm) metal transducer layer with a high coefficient of thermoreflectance at the probe wavelength. Advantages of TDTR include picosecond temporal resolution, the capability to resolve non-equilibrium dynamics among energy carriers, and, for some samples, improved sensitivity to thermal interface conductance and the thermal properties of thin films (P. E. Hopkins, et al., J. Heat Transfer 132, 081302 (2010)). On the other hand, FDTR avoids the complexity of a mechanical delay stage and the high cost of a pulsed laser system, and with the right range of modulation frequencies, FDTR has similar or improved sensitivity for many types of thin-film thermal measurements (J. Zhu, et al., J. Appl. Phys. 108, 094315 (2010); J. A. Malen, et al., J. Heat Transfer 133, 081601 (2011); J. Liu, et al., Rev. Sci. Instrum. 84, 034902 (2013); A. J. Schmidt, et al., J. Appl. Phys. 107, 104907 (2010)).

Previously, TDTR has been used for thermal conductivity imaging of materials (S. Huxtable, et al., Nature Mater. 3, 298 (2004); E. Lopez-Honorato, et al., J. Nucl. Mater. 378, 35 (2008)). However, this method, which is essentially single-frequency thermal wave imaging, is not self-contained because an average volumetric heat capacity has to be assumed for the entire sample, and in addition requires a careful choice of optical delay to minimize the effect of the transducer layer on the measurement. Similarly, photothermal beam deflection techniques have been used to image thermal diffusivity (B. Li, et al., J. Eur. Ceram. Soc. 19, 1631 (1999)). However, again thermal conductivity and heat capacity cannot be separated, and the spatial resolution is limited by the need to offset the probe beam relative to the pump beam. Therefore, there remains an important role for a high-resolution imaging technique able to simultaneously map different thermal properties.

SUMMARY

Thus far no one has been able to obtain a two-dimensional (2D) image of a thermophysical property or a set of thermophysical properties using FDTR with a limited number of modulation frequencies, such as 10, 9, 8, 7, 6, 5, 4, 3, or 2 modulation frequencies. Schmidt et al. demonstrated that when 30 modulation frequencies are used, a combination of thermal conductivity and heat capacity of a single spot on a sample can be determined (Review of Scientific Instruments 2009, 80, 094901); these measurements are time consuming due to the sheer number of modulation frequencies used, rendering it unrealistic to scan the sample surface to generate a 2D image of thermophysical properties of the sample. In Schmidt et al., 30 modulation frequencies were used for the purpose of collecting a set of data that allows for reliable curve fitting, from which the value of a desired thermophysical property is derived. And thus one skilled in the art would expect that reducing the number of modulation frequencies from 30 to mere 6 or less would not yield a set of data meaningful enough to permit reliable curve fitting. Further, this becomes more challenging when two or more thermophysical properties need to be determined simultaneously.

This challenge has been overcome by the technology disclosed herein, which is based in part, on the discovery that the number of modulation frequencies can be reduced significantly without compromising the data quality. In particular, it was found that a limited number of modulation frequencies can be properly selected based on the sensitivity of the optical properties (e.g, phase and/or amplitude) to the thermophysical properties at these frequencies. Provided herein are methods and apparatus for performing FDTR measurements on a sample, which permit the generation of 2D images of a thermophysical property or a set of thermophysical properties.

In one aspect of the technology described herein, a method of performing a frequency domain thermoreflectance measurement is provided, the method comprising the steps of (i) projecting a first beam of radiation onto a sample while a heat source is applied to the sample, wherein the heat source is modulated at a modulation frequency; (ii) measuring the reflected radiation from the first beam of radiation at at least two modulation frequencies simultaneously, wherein amplitude and/or phase data of the reflected radiation are obtained; (iii) repeating steps (i) and (ii) at a plurality of spots in the sample; and (iv) producing a two-dimensional (2D) image of at least one thermophysical property of the sample based on the measurements.

In one embodiment, the measurement is at three modulation frequencies simultaneously.

In one embodiment, the measurement is at four modulation frequencies simultaneously.

In one embodiment, the measurement is at five modulation frequencies simultaneously.

In one embodiment, the measurement is at six modulation frequencies simultaneously.

In one embodiment, the heat source is produced or provided by a second beam of radiation projected onto the sample.

In one embodiment, the second beam of radiation is aligned coaxially with the first beam of radiation.

In one embodiment, the modulation frequencies are determined from sensitivity of amplitude and/or phase of the reflected radiation to a given thermophysical property.

In one embodiment, one modulation frequency is at or near maximum sensitivity to the given thermophysical property.

In one embodiment, the modulation frequencies are spaced to fit a desired set of thermophysical properties using a sensitivity function.

In one embodiment, the second beam of radiation is modulated via a sine wave for each modulation frequency.

In one embodiment, the modulation frequencies are in the range of 1 kHz to 50 MHz.

In one embodiment, the measurement is done using a lock-in amplifier.

In one embodiment, the method further comprises moving the sample relative to the first beam of radiation, thereby scanning the first beam of radiation across the sample.

In one embodiment, the thermophysical property is determined fitting of data obtained from the measurement.

In one embodiment, the thermophysical property is selected from the group consisting of film thickness, density, heat capacity, thermal conductivity, in-plane thermal conductivity, cross-plane thermal conductivity, and thermal interface conductance.

In one embodiment, the method comprises producing a 2D image of two or more thermophysical properties of the sample.

In one embodiment, the two or more thermophysical properties are in-plane thermal conductivity and cross-plane thermal conductivity.

In one embodiment, the sample is a bulk sample or a multilayered sample.

In one embodiment, the sample is coated with a layer of metal.

In one embodiment, the 2D image exhibits a maximum spatial resolution of about 200 nm.

In one embodiment, the first beam of radiation is a laser beam.

In one embodiment, the second beam of radiation is a laser beam.

BRIEF DESCRIPTION OF THE DRAWINGS

(FIG. 7A) 100 nm gold film on a fused silica substrate, (FIG. 7B) 100 nm gold film on a sapphire sample, (FIG. 7C) 100 nm gold film on a single crystal quartz sample, and (FIG. 7D) 240 nm silicon thin film on a fused silica substrate covered by 100 nm gold film.

(FIG. 11A) Thermal interface conductance map. (FIG. 11B) Numerical values for interface conductance across the path shown by the dashed line in FIG. 11A. (FIG. 11C) Substrate thermal conductivity map. (FIG. 11D) Numerical values for the substrate thermal conductivity across the path shown by the dashed line in FIG. 11C.

(FIG. 12A) Thermal interface conductance map obtained with a 1.7 µm pump radius and a 0.75 µm probe radius. (FIG. 12B) Cross-sectional image of FIG. 12A. (FIG. 12C) Thermal interface conductance map obtained with a 9.2 µm pump radius and a 0.75 µm probe radius. (FIG. 12D) Cross-sectional image of FIG. 12C.

FIGS. 19A-19C show phase image comparison between flake 1 and flake 2.

FIG. 19A is a phase image of flake 1 at 7.1 MHz.
FIG. 19B is a phase image of flake 2 at 7.1 MHz.

FIG. 19C is a plot of phase profiles along the two dashed lines in FIG. 19A and FIG. 19B, showing enhanced sensitivity to radial transport in graphene due to the low thermal conductivity of the Ti film.

FIGS. 20A-20F are thermal conductance maps of the two samples.

FIG. 20A is a $G_\parallel$ map of flake 1.

FIG. 20B is a set of histograms of the thermal conductivity for single-layer graphene and bi-layer graphene analyzed from the polygons in FIG. 20A. The solid red lines are normal distribution fits.

FIG. 20C is a TBC map of flake 1. The upper limit of the color bars is set at 50 MW $m^{-2}$ $K^{-1}$ to highlight the graphene flake, although the measured value of TBC for Au/Ti/$SiO_2$ for this sample was closer to 100 MW $m^{-2}$ $K^{-1}$.

FIG. 20D is a set of histograms of TBC of single-layer graphene and bi-layer graphene, analyzed from the polygons in FIG. 20C. The solid curves are normal distribution fits.

FIG. 20E is a $G_\parallel$ map of flake 2.
FIG. 20F is a TBC map of flake 2.

DETAILED DESCRIPTION

Figure 1:
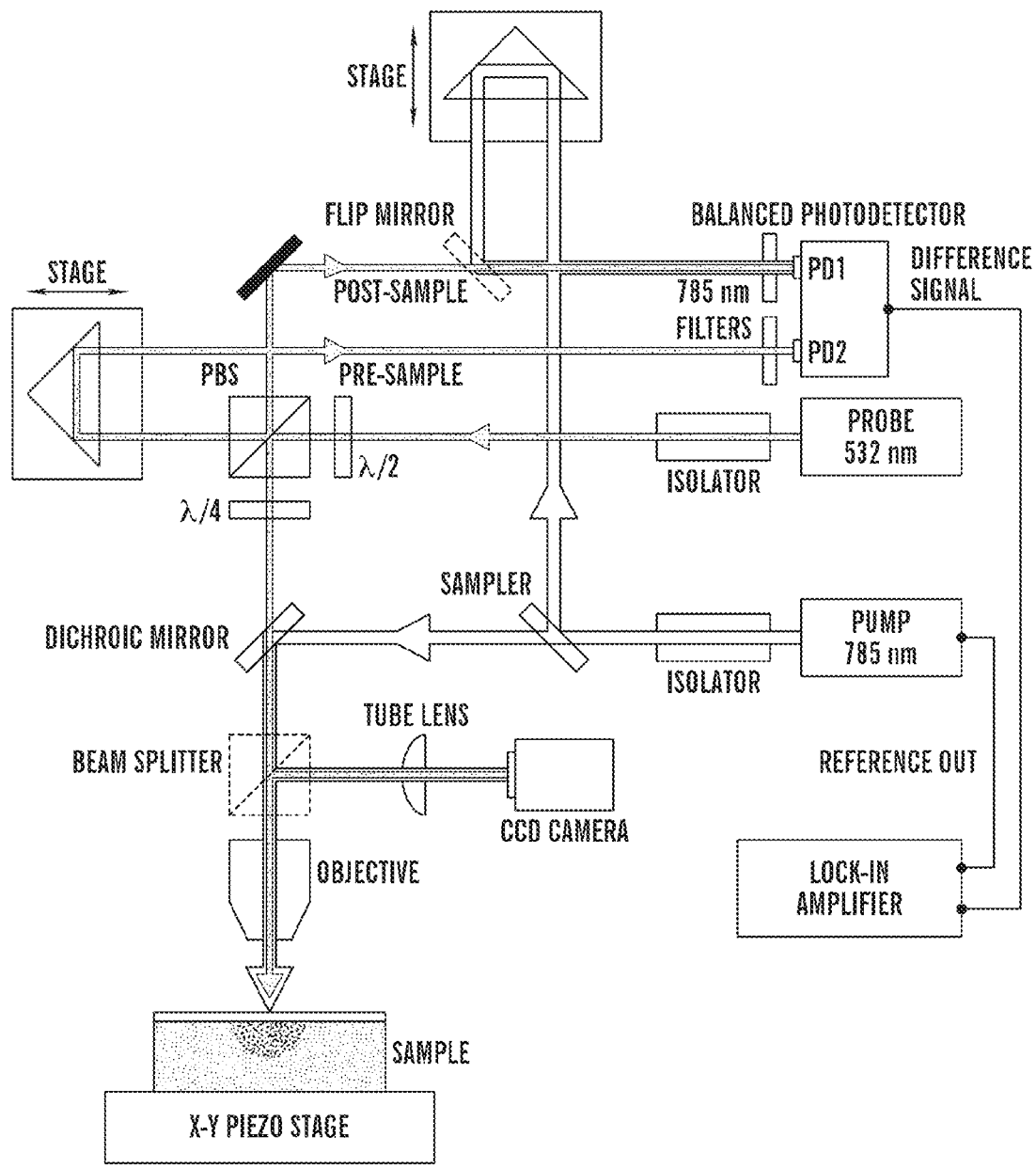
FIG. 1 is a schematic of a FDTR microscope based on two continuous wave (cw) diode lasers. A pump laser is directly modulated by the reference output signal from a lock-in amplifier. The lock-in detects the phase lag in the probe signal at the modulation frequency relative to the reference output signal. A balanced photodetection scheme is used to improve the signal to noise ratio. A flip mirror is used to temporarily direct a portion of the pump beam to the signal photodiode PD1 and determine the absolute phase of the pump beam at the sample surface.

In a thermoreflectance measurement, the optical properties of a beam of radiation reflected from a sample can be altered when a heat source is applied to the sample, due to the change in the reflectance of the sample surface. From the change in optical properties, quantitative information about one or more thermophysical properties of the sample can be derived. As used herein, the term "thermophysical property" refers to either the physical characteristics or thermal property of a sample. For example, without limitation, the thermophysical property can be film thickness, density, heat capacity, thermal conductivity, in-plane thermal conductivity, cross-plane thermal conductivity, thermal interface conductance, coefficient of thermal expansion, and/or thermal boundary conductance.

More specifically, the technology described herein is related to frequency domain thermoreflectance (FDTR), as opposed to time domain thermoreflectance (TDTR). In FDTR, as the heat source is modulated periodically with a modulation frequency, the reflected beam of radiation is measured at a plurality of modulation frequencies (e.g., 2, 3, 4, 5, 6, 7, 8, 9, 10, or more) simultaneously. The technology described herein takes advantage of the discovery that the number of modulation frequencies can be reduced significantly without compromising the data quality, and as a result measurement time can also be significantly reduced. By reducing the number of modulation frequencies from 30 to 6 or less, the measurement time can be cut significantly, depending on the measurement device. In a particular example, when a 6-channel lock-in amplifier is used as the measurement device, the measurement time for 6 modulation frequencies is less than 20% of the measurement time required for 30 modulation frequencies. In this context, the selection of modulation frequencies presents a challenge in that the ability to obtain meaningful data would be more significantly affected by some smaller subsets of modulation frequencies than others.

In the approaches described herein, it was found that a limited number of modulation frequencies can be properly selected based on the sensitivity of the optical properties (e.g. phase and/or amplitude) to the thermophysical properties at these frequencies, and that when modulation frequencies selected in such manner are used, high quality 2D images can be produced despite the sharply narrowed data sets. Thus, the significant reduction in measurement time in turn permits FDTR measurements across substantially the entire sample surface or a portion thereof, permitting the generation of a 2D image of thermophysical properties of the sample.

The methods and apparatus described herein can be used, e.g., for both thermal characterizations of electronic, optoelectronic, and/or photonic devices, both at the surfaces and within an operating device. The methods and apparatus described herein permit the production of 2D images of 1, 2, 3, or more thermophysical properties of a sample. For example, samples can include, but are not limited to, photonic and optoelectronic devices (e.g., lasers, optical amplifiers, photovoltaic cells, solar cells, etc.), and electronics (e.g., transistors, integrated circuits, supercapacitors, batteries, etc.). Application to electronic devices and circuits includes characterization of hot spots, defects, or other performance markers. It can also be applied to general characterizations of materials and structures, including mapping thermal conductance and/or heat capacity, identifying defects or delaminations, locating subsurface cracks, or identifying inclusions or contaminants.

Accordingly, in one aspect of the technology described herein, a method of performing a frequency domain thermoreflectance imaging is provided, the method comprising the steps of (i) projecting a first beam of radiation onto a sample while a heat source is applied to the sample, wherein the heat source is modulated at a modulation frequency; (ii) measuring the reflected radiation from the first beam of radiation at at least two modulation frequencies simultaneously, wherein amplitude and/or phase data of the reflected radiation are obtained; (iii) repeating steps (i) and (ii) at a plurality of spots in the sample; and (iv) producing a two-dimensional (2D) image of at least one thermophysical property of the sample based on the measurements.

The heat source can be produced by the first beam of radiation or a portion thereof, or an external source such as a second beam of radiation absorbed by the sample, an electrical current applied to the sample, temperature changes of the sample mount, and inductive heating. In one embodiment, such a second beam of radiation, also referred herein as the pump beam, can be aligned coaxially with the first beam of radiation (also referred herein as the probe beam). The coaxial alignment of the two beams permits that the probe beam is reflected from the same spot heated by the pump beam.

The heat source can produce a temperature change of the sample surface. For example, the temperature change can be in the range of 0.1° C. to 5° C.

In one embodiment, the heat source is periodic. In one embodiment, the heat source has a Gaussian distribution profile. In some embodiments of the pump beam being the heat source, the Gaussian distribution profile determines the spot size of the pump beam.

In some embodiments, the heat source can be modulated via a waveform at at least one modulation frequency. The waveform can be generated by a waveform generator, which is available commercially. Without limitation, the waveform can be a sine wave, a square wave, a triangle wave, a sawtooth wave, or a combination thereof. When two or more modulation frequencies are used simultaneously to modulate the heat source (e.g., a pump beam), a composite signal comprising the sum of two or more waveforms, each of which corresponding to one modulation frequency, is created to control the waveform generator. For example, when six modulation frequencies are used simultaneously, the composite signal can be the sum of six sine waves.

In some embodiments, the reflected radiation from the first beam of radiation is measured at 2 to 20 modulation frequencies simultaneously, 2 to 18 modulation frequencies simultaneously, 2 to 16 modulation frequencies simultaneously, 2 to 14 modulation frequencies simultaneously, 2 to 12 modulation frequencies simultaneously, 2 to 10 modulation frequencies simultaneously, 2 to 9 modulation frequencies simultaneously, 2 to 8 modulation frequencies simultaneously, 2 to 7 modulation frequencies simultaneously, 2 to 6 modulation frequencies simultaneously, 2 to 5 modulation frequencies simultaneously, or 2 to 4 modulation frequencies simultaneously.

In some embodiments, the reflected radiation from the first beam of radiation is measured at at least 3 modulation frequencies simultaneously, or at least 4 modulation frequencies simultaneously. In some embodiments, the reflected radiation from the first beam of radiation is measured at no more than 20 modulation frequencies simultaneously, no more than 18 modulation frequencies simultaneously, no more than 16 modulation frequencies simultaneously, no more than 14 modulation frequencies simultaneously, no more than 12 modulation frequencies simultaneously, no more than 10 modulation frequencies simultaneously, no more than 9 modulation frequencies simultaneously, no more than 8 modulation frequencies simultaneously, no more than 7 modulation frequencies simultaneously, or no more than 6 modulation frequencies simultaneously.

Generally, fewer modulation frequencies tend to result in faster imaging speed. However, fewer modulation frequencies can also lead to inaccurate data fitting. Using methods described herein, the number of modulation frequencies can be selected to achieve a desirable trade-off between imaging speed and the reliability of data fitting.

In a preferred embodiment, the modulation frequencies can be determined from the sensitivity of the optical properties such as amplitude or phase of the reflected radiation to a given thermophysical property. The sensitivity is a function of frequency, which indicates how sensitive an optical property of the reflected radiation is to a given thermophysical property in a range of frequencies. The sensitivity can be calculated prior to the measurements to provide a guide for the selection of modulation frequencies. See Schmidt et al., Review of Scientific Instrument, 2009, 80, 094901, the contents of which are incorporated by reference in their entirety.

For example, a sensitivity function $S_x(\omega)$ can be used, which describes how a change in a parameter x in a thermal model affects the phase signal or amplitude signal as a function of frequency. The thermal model is described in detail in Schmidt et al., Review of Scientific Instrument, 2009, 80, 094901. Using this model, the sensitivity of the thermal phase signal to various thermophysical properties can be computed as a function of modulation frequency. The sensitivity function can be presented in the form of a plot, for example, as shown in FIGS. 7A-7D, in which the peak and valley of a curve each represents maximum sensitivity. As used herein, the term "maximum", when used to describe sensitivity, refers to the absolute number. For example, a largest negative phase change is regarded as a maximum. The term can mean local maximum or global maximum depending on the context. In some embodiments, both local maximum sensitivity and global maximum sensitivity are used. In some embodiments, only global maximum sensitivity is used. In some embodiments, only local maximum sensitivity is used.

In one embodiment, the modulation frequencies are spaced to fit a desired set of thermophysical properties using the sensitivity function. In one embodiment, at least one modulation frequency is at or near the maximum sensitivity to the given thermophysical property. In one embodiment, 2, 3, or more modulation frequencies are at or near the maximum sensitivity to the given thermophysical property. A modulation frequency is considered to be near the maximum sensitivity if it is within about ±20% of the maximum sensitivity. In one embodiment, one modulation frequency is at which the phase or amplitude of the reflected radiation is indifferent or insensitive to the given thermophysical property.

In one embodiment, when FDTR measurements are performed to obtain images for a set of thermophysical properties (e.g., 2, 3, 4, 5, or more), at least one modulation frequency can be selected to be at or near the maximum sensitivity to each thermophysical property. Preferably, at least two modulation frequencies are selected to be at or near the maximum sensitivity to each thermophysical property. Non-limiting examples of a set of thermophysical properties include heat capacity and the thermal conductivity, in-plane and cross-plane thermal conductivities in-plane thermal conductivity and the film thickness, and film thickness and thermal conductivity.

Factors affecting the selection of modulation frequency include, but are not limited to, the material composition of the sample, the given thermophysical property, the probe beam spot size, and the pump beam spot size. The modulation frequency can be up to a few hundred MHz, for example, in the range of 500 Hz to 300 MHz, 1 kHz to 200 MHz, 1 kHz to 100 MHz, or 4 kHz to 50 MHz.

In one embodiment, the measurement is done using a lock-in amplifier. A lock-in amplifier (also known as a phase-sensitive detector) is a type of amplifier that can extract a signal with a known carrier wave from an extremely noisy environment. Preferably, the number of channels in the lock-in amplifier is equal to or greater than the number of modulation frequencies used in the FDTR measurements. In one embodiment, the lock-in amplifier can measure the phase shift or phase change of the reflected radiation. In one embodiment, the lock-in amplifier can measure the amplitude change of the reflected radiation. In one embodiment, the lock-in amplifier can measure both the phase shift and amplitude change of the reflected radiation. In some embodiments of phase shift being measured, the method further comprises subtracting from the measured phase shift, a net external phase introduced by the system, such as optical paths and electronic components.

In one embodiment, the phase measured by the lock-in amplifier can be given by $$\phi_{LI} = \tan^{-1}\frac{\Im(H(\omega))}{\Re(H(\omega))} + \phi_{ext},$$

where $H(\omega)$ is a complex number that represents the frequency response of the sample surface temperature to a periodic heat flux, and $\varphi_{ext}$ is the net external phase.

Figure 9A:
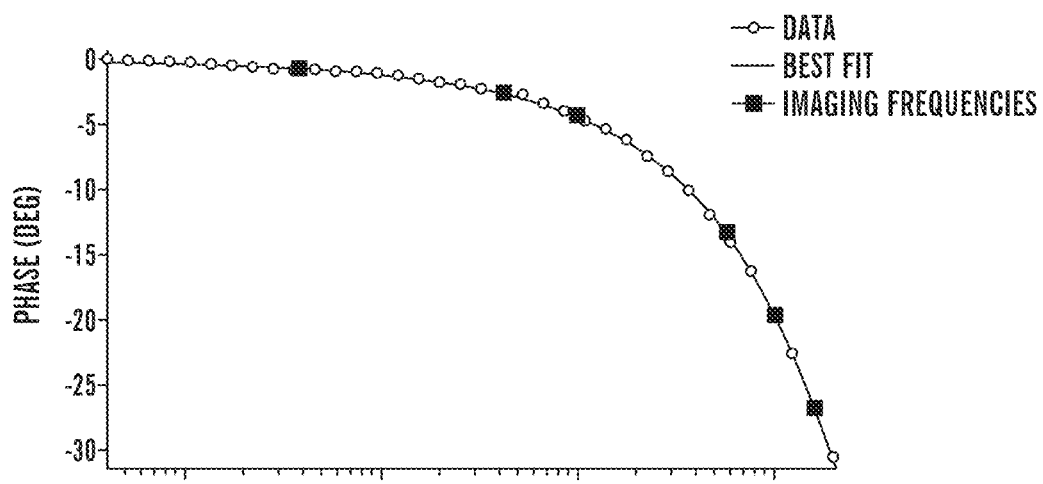
FIG. 9A is a plot showing FDTR measurement of the sample in a region without titanium, and best model fit. Squares indicate the six frequencies used for imaging.

In one embodiment, the method further comprises moving the sample relative to the probe beam, thereby scanning the probe beam across the sample surface or a portion thereof. The scanning can be a raster scan. The data obtained from the measurements at a plurality of spots are fitted to the thermal model to quantitatively determine the value of a thermophysical property. FIG. 9A shows one example of data fitting. In this particular example, even though six modulation frequencies only yield six data points, they are meaningful enough for reliable data fitting to extract useful information, as a result of proper selection of the frequencies as described herein. Data fitting is done for each spot or pixel individually, and the results of the data fitting are pieced together to produce a 2D image or map. In one embodiment, an image or a set of images is produced for two or more thermophysical properties of the sample, such as in-plane thermal conductivity and cross-plane thermal conductivity.

The 2D images generated by the methods described herein exhibit a maximum spatial resolution of 100 nm to 300 nm, 100 nm to 250 nm, or 150 nm to 250 nm. Improvement in lateral resolution can be obtained, for example, by reducing the beam spot sizes. Beam spot size can be reduced by using light with shorter wavelength (e.g., blue or ultraviolet lasers) or an objective lens with a higher numerical aperture (e.g., 100× or higher).

Figure 23:
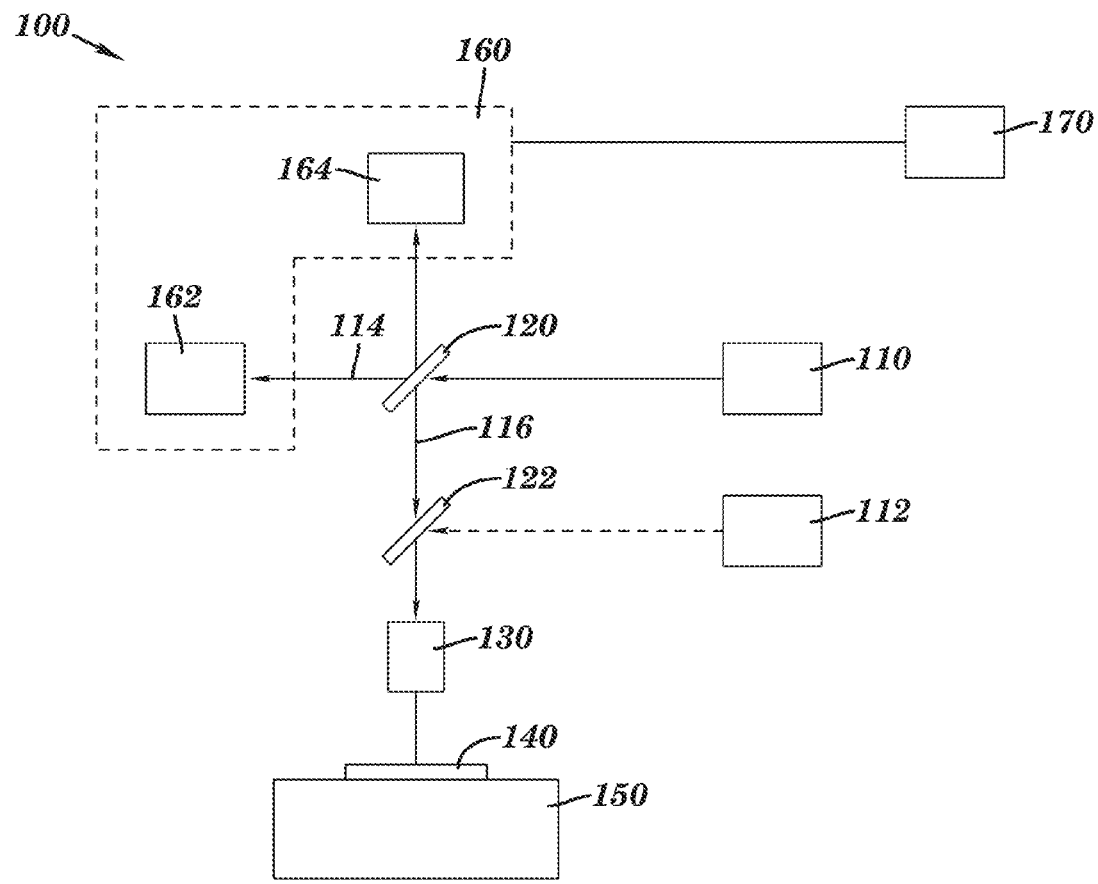
FIG. 23 is a schematic of an apparatus 100 according to some embodiments of the technology described herein.

FIG. 23 schematically illustrates an embodiment of an apparatus 100 for performing the methods described herein. Apparatus 100 comprises a first light source 110 for producing a first beam of radiation (i.e., the probe beam), a second light source 112 for producing a second beam of radiation (i.e., the pump beam), a beam splitter 120 for splitting the probe beam into two portions, a dichroic mirror 122, an objective lens 130 for projecting the beams on to a sample 140, a moving stage 150 for moving the sample 140, a photodetection system 160, and a measurement system 170.

The probe beam is split by the beam splitter 120 (e.g., a polarizing beam splitter) into two portions: a first portion 114 is measured by a first photodetector 162 of the photodetection system 160 without interacting with the sample 140; and a second portion 116 is projected onto the sample 140 through the objective lens 130. At the same time, the pump beam is reflected from the dichroic mirror 122 and projected onto the sample 140 through the objective lens 130. The dichroic mirror 122 permits the probe beam to pass through with minimal reflection and the pump beam to be primarily reflected. The pump beam is modulated at a particular frequency to create a periodic heat flux on the sample surface. The second portion 116 of the probe beam is reflected from the sample 140 back into the objective lens 130 and measured by a second photodetector 164 of the photodetection system 160.

The photodetection system 160 comprises a first photodetector 162 and a second photodetector 164. In one embodiment, the photodetection system 160 is a balanced photodetector. Balanced photodetection is known to improve the signal-to-noise ratio at low frequencies. For example, balanced photodetection can be realized when two photodiodes are connected such that their photocurrents cancel. The measurement system 170 can receive a detection signal from the photodetection system 160. Optionally, the measurement system 170 can receive a reference signal from the second light source 112. In one embodiment, the measurement system 170 is a lock-in amplifier. The reference signal permits the lock-in amplifier to reliably obtain amplitude or phase data even when the signal-to-noise ratio is low. The operational principles of lock-in amplifiers are known in the art and are not discussed in detail here.

Apparatus 100 can further comprise other optics components such as half-wave plates, quarter-wave plates, flip mirrors, filters, isolators, tube lens, CCD cameras, translation stages, and samplers. The functions of these optics components in an apparatus for FDTR imaging would be apparent for a skilled artisan.

Relative motion between the sample 140 and the objective lens 130 permits a 2D image to be obtained. It should be noted that during the relative motion, the spacing between the objective lens 130 and the sample surface should be such that the sample surface remains within the depth of focus of the objective lens 130. Relative motion can be achieved by the use of the moving stage 150. The moving stage 150 can determine the scanning range and step size of the movement. Examples of moving stages include, but are not limited to, piezo stages and stepper motors. In one embodiment, the sample is placed on a moving stage. In another embodiment, the apparatus is placed on a moving stage.

The probe beam can be aligned coaxially with the pump beam and focused with the pump spot to monitor the periodic fluctuations in reflectivity at the sample surface caused by the oscillating sample temperature. The coaxial geometry simplifies alignment and permits diffraction-limited beam spot profiles. The probe beam and pump beam can be produced from a variety of light sources. Exemplary light sources include, but are not limited to, lasers (e.g., pulsed or continuous wave laser), light-emitting diodes, and lamps. In a preferred embodiment, the probe beam is a laser beam and the pump beam is a laser beam. The wavelengths of the probe beam and pump beam can be selected independently. The wavelengths are chosen to match the top surface material of the sample. The pump beam wavelength should be strongly absorbed at the surface, and the probe beam should be at a wavelength where the coefficient of thermoreflectance is large. For example, for metal coatings like aluminum or gold, most visible wavelengths are strongly absorbed and work well for the pump beam. The probe beam wavelength is more selective because thermoreflectance has a strong peak for most materials (for example 785 nm for aluminum or 532 nm for gold). The wavelengths of the pump beam and probe beam should also be somewhat different (e.g., 10 nm or more) so that they can be separated with color filters.

The spot radii of the pump beam and probe beam are sensitive parameters in the thermal model. The spot radii can be tuned, for example, by using an objective lens with a different magnification factor. The spot radii can be determined by methods such as a 2D knife-edge technique.

The type of photodetector used is not critical to the function of the apparatus described herein. A photodetector that can achieve high signal-over-noise ratio is desirable. Exemplary photodetectors include, but are not limited to, a fluorometer, a charge coupled device, a photodiode, a photo multiplier tube, a spectrophotometer, a scanning detector, an avalanche photodetector, and a galvo-scanner. The photodetector can transmit signals that express characteristics of resultant signals received. For example, the photodetector can be in communication with an output device, such as an analog or digital gauge, that displays a value proportional to resultant signal intensity. The detector can be in communication with a computer through a data transmission line to transmit analog or digital signals for display, storage, evaluation, correlation, and the like.

A computer can be used to control one or more components of the apparatus and receive signals for processing. For example, the computer can control the pump beam and/or heat source (e.g., the probe beam); the computer can also control the stage that moves the sample or the apparatus; the computer can receive and process signals from the photodetectors. The computer can be, e.g., a PC (Intelx86 or Pentium chip-compatible with DOS®, OS2®, WINDOWS® operating systems) a MACINTOSH®, Power PC, or SUN® work station (compatible with a LINUX or UNIX operating system) or other commercially available computer which is known to one of skill. The computer can be, e.g., a simple logic device, such as an integrated circuit or processor with memory, integrated into the system. Software for interpretation of detector signals is available, or can easily be constructed by one of skill using a standard programming language such as C, Visualbasic, Fortran, Basic, Java, or the like.

Figure 13B:
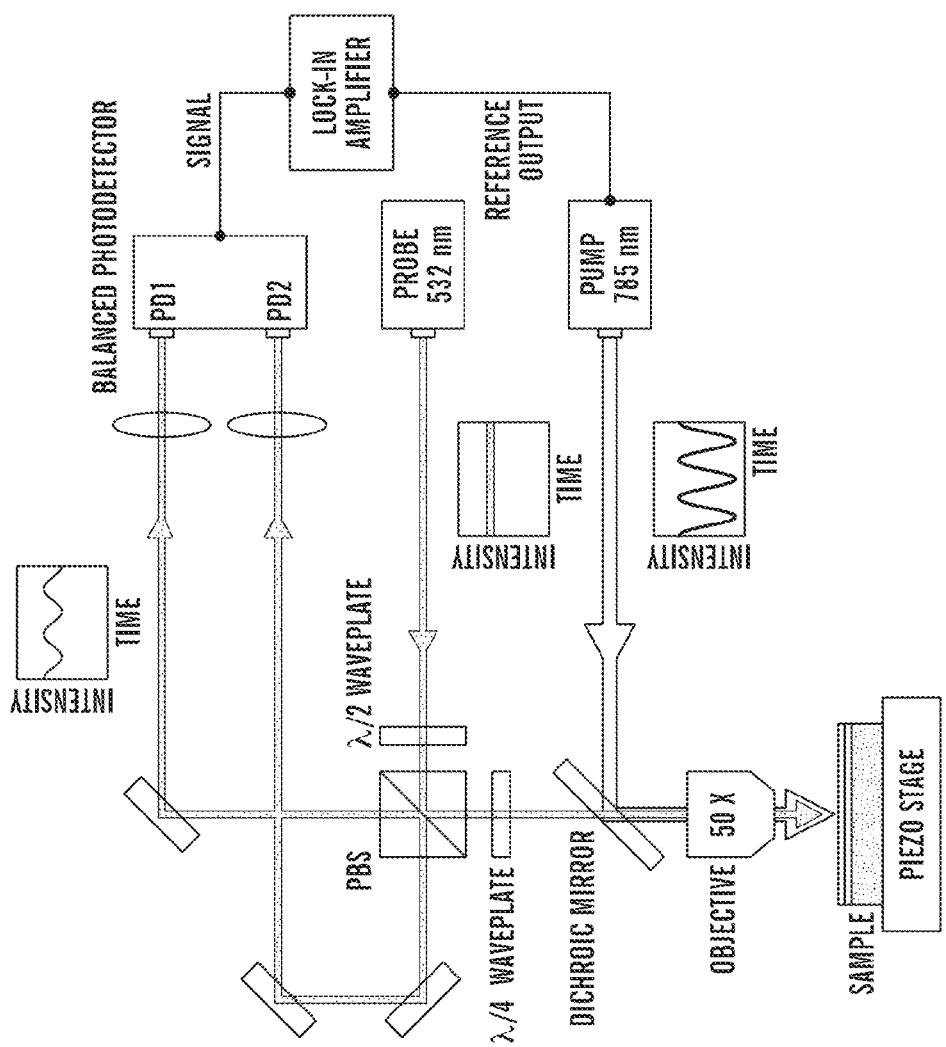
FIG. 13B is a schematic of the FDTR microscope used in the experiments. A digitally modulated pump laser heats the sample while a probe beam monitors the surface reflectivity. A balanced photodetector is used to improve the signal to noise ratio. A piezo stage is used to raster scan the sample for imaging.

FIG. 1 and FIG. 13B also schematically illustrate some embodiments of the FDTR microscope.

The methods and/or apparatus described herein can be used to measure a variety of samples. The sample can be a bulk sample or a multilayered sample. The sample can comprise nanoscale materials (e.g., nanoparticles, nanowires, nanotubes, or graphenes) or microfabricated structures (e.g., electronic structures such as electrodes, fluidic structures such as microchannels, or photonic structures such as waveguides and ring resonators) disposed thereon. The sample can be a microelectronic device such as an integrated circuit, a nanoelectronic device, a photonic device, or an optoelectronic device. In one embodiment, the sample surface can be made more reflective by coating it with a layer with a high coefficient of thermoreflectance at the probe wavelength, such as a metal layer (e.g., gold, silver, platinum, copper, titanium, chromium, etc.). The thickness of the layer should depend on, among other things, the particular sample and thermophysical property. For example, the layer can be about 1 nm to 200 nm thick. The FDTR imaging technology described herein can image the features on the sample surface, or features that are buried underneath the sample surface.

All embodiments of the technology described herein can be described through functional modules, which are defined by computer executable instructions recorded on computer readable media and which cause a computer to perform method steps when executed. The modules have been segregated by function for the sake of clarity. However, it should be understood that the modules need not correspond to discrete blocks of code and the described functions can be carried out by the execution of various code portions stored on various media and executed at various times.

In some embodiments, the technology described herein provides a system for imaging at least one thermophysical property of a sample, the system comprising (a) a determination module configured to determine optical information, wherein the optical information comprises phase and/or amplitude data of the reflected probe beam at at least two modulation frequencies simultaneously; (b) a storage device configured to store data output from the determination module; (c) a processing module adapted to process the data stored on the storage device and produce a retrieved content, wherein the data processing comprises fitting the data to a thermal model; and (d) a display module for displaying a page of the retrieved content for the user on the client computer, wherein the retrieved content is an image of at least one thermophysical property of the sample.

In some embodiments, the technology described herein provides a computer program comprising a computer readable media or memory having computer readable instructions recorded thereon to define software modules including a determination module and a processing module for implementing a method on a computer, said method comprising (a) determining with the determination module optical information, wherein the optical information comprises phase and/or amplitude data of the reflected probe beam at at least two modulation frequencies simultaneously; (b) storing data output in a storage device from the determination module; (c) processing with the processing module the data stored on the storage device, wherein the processing comprises fitting the data to a thermal model and producing a retrieved content; and (d) displaying a page of the retrieved content for the user on the client computer, wherein the retrieved content is an image of at least one thermophysical property of the sample.

The "computer readable medium" can include data and computer-executable instructions for performing the steps of the method of the invention. Suitable computer readable media include floppy disk, CD-ROM/DVD/DVD-ROM, hard-disk drive, flash memory, ROM/RAM, magnetic tapes and etc. The computer executable instructions can be written in a suitable computer language or combination of several languages.

In some aspects, the functional modules of embodiments of the invention include a determination module, a storage device, a processing module, and a display module.

The determination module can include computer executable instructions to determine and provide optical information using an optical instrument. As used herein, an "optical instrument" refers to any instrument that either processes light waves to enhance an image for viewing, or analyzes light waves (or photons) to determine one of a number of characteristic optical properties. Known determination modules for determining optical properties include, for example, but are not limited to, microscopes, cameras, interferometers (for measuring the interference properties of light waves), photometers (for measuring light intensity); polarimeters (for measuring dispersion or rotation of polarized light), reflectometers (for measuring the reflectivity of a surface or object), refractometers (for measuring refractive index of various materials), spectrometers or monochromators (for generating or measuring a portion of the optical spectrum, for the purpose of chemical or material analysis), autocollimators (used to measure angular deflections), and vertometers (used to determine refractive power of lenses such as glasses, contact lenses and magnifier lens). FIGS. 1, 13B, and 23 show exemplary embodiments of a determination module.

The optical information determined in the determination module can be read by the storage device. A variety of software programs and formats can be used to store the optical information on the storage device. Any number of data processor structuring formats (e.g., text file or database) can be employed to obtain or create a medium having the information recorded thereon.

By providing optical information in computer-readable form, one can process the optical information to produce a retrieved content. A page of the retrieved content can then be displayed through a "display module".

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

paragraph 1. A method of performing a frequency domain thermoreflectance measurement, the method comprising:
(i) projecting a first beam of radiation onto a sample while a heat source is applied to the sample, wherein the heat source is modulated at a modulation frequency;
(ii) measuring the reflected radiation from the first beam of radiation at at least two modulation frequencies simultaneously, wherein amplitude and/or phase data of the reflected radiation are obtained;
(iii) repeating steps (i) and (ii) at a plurality of spots in the sample; and
(iv) producing a two-dimensional (2D) image of at least one thermophysical property of the sample based on the measurements.

paragraph 2. The method of paragraph 1, wherein the measurement is at three modulation frequencies simultaneously.

paragraph 3. The method of paragraph 1, wherein the measurement is at four modulation frequencies simultaneously.

paragraph 4. The method of paragraph 1, wherein the measurement is at five modulation frequencies simultaneously.

paragraph 5. The method of paragraph 1, wherein the measurement is at six modulation frequencies simultaneously.

paragraph 6. The method of paragraph 1, wherein the heat source is produced by a second beam of radiation projected onto the sample.

paragraph 7. The method of paragraph 6, wherein the second beam of radiation is aligned coaxially with the first beam of radiation.

paragraph 8. The method of paragraph 1, wherein the modulation frequencies are determined from sensitivity of amplitude and/or phase of the reflected radiation to a given thermophysical property.

paragraph 9. The method of paragraph 8, wherein one modulation frequency is at or near maximum sensitivity to the given thermophysical property.

paragraph 10. The method of paragraph 1, wherein the modulation frequencies are spaced to fit a desired set of thermophysical properties using a sensitivity function.

paragraph 11. The method of paragraph 6, wherein the second beam of radiation is modulated via a sine wave for each modulation frequency.

paragraph 12. The method of paragraph 1, wherein the modulation frequencies are in the range of 1 kHz to 50 MHz.

paragraph 13. The method of paragraph 1, wherein the measurement is done using a lock-in amplifier.

paragraph 14. The method of paragraph 1, further comprising moving the sample relative to the first beam of radiation, thereby scanning the first beam of radiation across the sample.

paragraph 15. The method of paragraph 1, wherein the thermophysical property is determined through fitting of data obtained from the measurement.

paragraph 16. The method of paragraph 1, wherein the thermophysical property is selected from the group consisting of film thickness, density, heat capacity, thermal conductivity, in-plane thermal conductivity, cross-plane thermal conductivity, and thermal interface conductance.

paragraph 17. The method of paragraph 1, comprising producing a 2D image of two or more thermophysical properties of the sample.

paragraph 18. The method of paragraph 17, wherein the two or more thermophysical properties are in-plane thermal conductivity and cross-plane thermal conductivity.

paragraph 19. The method of paragraph 1, wherein the sample is a bulk sample or a multilayered sample.

paragraph 20. The method of paragraph 19, wherein the sample is coated with a layer of metal.

paragraph 21. The method of paragraph 1, wherein the 2D image exhibits a maximum spatial resolution of about 200 nm.

paragraph 22. The method of paragraph 1, wherein the first beam of radiation is a laser beam.

paragraph 23. The method of paragraph 6, wherein the second beam of radiation is a laser beam.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

As used herein, the terms "phase shift" and "phase change" are used interchangeably to describe the change in phase that occurs when a beam of radiation is reflected from a sample surface or device.

As used herein, the term "amplitude" refers to the amplitude of the measured signal, which is directly proportional to the magnitude of the oscillation of the surface temperature of the sample. It is also proportional to the magnitude of the oscillation of the probe beam (which is an electromagnetic wave) via the coefficient of thermoreflectance. In some embodiments, the amplitude is related to the amplitude of the surface temperature, for example, in a proportional relationship.

As used herein the "storage device" is intended to include any suitable computing or processing apparatus or other device configured or adapted for storing data or information. Examples of storage devices suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The data is typically provided in digital form that can be transmitted and read electronically, e.g., via the Internet, on diskette, or any other mode of electronic or non-electronic communication.

As used herein, "stored" refers to a process for storing information on the storage device such that it can be read back from the device. Those skilled in the art can readily adopt any of the presently known methods for recording information on known media to generate manufactures comprising the sequence information or expression level information.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology disclosed herein is further illustrated by the following examples which in no way should be construed as being further limiting.

Example 1: Thermal Property Microscopy with Frequency Domain Thermoreflectance

Without the need for a variable optical delay, FDTR lends itself to rapid raster scanning of the sample while multiple frequencies are excited simultaneously. In this sense, imaging FDTR can be considered a specific form of thermal wave imaging (ref. 14), in which the response of a sample to a periodic heat source may be detected through a variety of mechanisms and used to infer various physical properties.

By fitting the phase of the thermal wave at the sample surface in different frequency regimes, FDTR can reliably extract multiple combinations of geometrical and thermal properties. For example, in bulk samples it can be used to measure the heat capacity and the thermal conductivity, or both the in-plane and cross-plane thermal conductivities of anisotropic samples (ref. 8). Additional possible combinations include the in-plane thermal conductivity and the thickness of thin films (ref. 13), and the thickness and thermal conductivity of buried layers (ref 9). With imaging FDTR, spatial maps of all these combinations with micrometer-scale resolution can be simultaneously created.

Experimental Setup

FDTR can be implemented with either a pulsed laser source with a high-frequency pulsing rate, such as an 80 MHz Ti:sapphire laser oscillator, or with two continuous-wave (cw) lasers (ref 8). The former is convenient for doing FDTR measurements with a typical TDTR system, while the latter is significantly less expensive and allows the pump and probe wavelengths to be chosen independently, and also permits compact fiber-based systems (10). The experimental system used herein, shown in FIG. 1, is based on two TEMOO free space cw lasers. The pump is a 50 mW diode laser with a wavelength of 785 nm which is digitally modulated by the reference output of the lock-in amplifier (Zurich Instruments HF2LI), and the probe is a 20 mW diode laser with a wavelength of 532 nm. Each beam passes through an optical isolator to eliminate back reflection and improve power stability.

The pump beam is reflected by a dichroic mirror and focused onto the sample with a microscope objective, creating a periodic heat flux with a Gaussian spatial distribution on the sample surface. The probe beam is aligned coaxially with the pump beam and focused with the pump spot to monitor the periodic fluctuations in reflectivity at the sample surface caused by the oscillating sample temperature. The coaxial geometry simplifies alignment and permits diffraction-limited beam spot profiles. The sample is coated with a thin metal film, on the order of 50-100 nm, which is chosen to maximize the coefficient of thermoreflectance at the probe wavelength (ref. 18). For the system described herein, gold gives a large signal at the 532 nm probe wavelength. The sample is mounted on a piezoelectric translation stage with an 80 μm scanning range in the x and y directions and a step size of 0.2 nm.

Balanced photodetection was used to improve the signal-tonoise ratio at low frequencies. This is implemented with a balanced photodetector (Thorlabs PDB410A) comprised of two well-matched photodiodes PD1 and PD2. The probe beam is split with a polarizing beam splitter (PBS). One beam (postsample) is focused onto the sample and reflected back to PD1, while the other beam (pre-sample) is sent along a matched optical path to PD2. The output currents of PD1 and PD2 are subtracted in the detector and sent through a low-noise transimpedance amplifier, removing common mode noise in the probe beam. Fine balancing is performed by adjusting the half waveplate until the noise is minimized. A translation stage is used to precisely match the optical path lengths of the presample and post-sample beams for maximum noise rejection. Two bandpass filters (Thorlabs FGB37) are placed before the photodetectors to block scattered pump light, which would otherwise overwhelm the thermal signal.

In the implementation of FDTR, the phase lag of the post-sample probe beam, measured with respect to the reference signal from the lock-in amplifier, is compared against the calculated phase lag of the sample surface temperature to a periodic Gaussian heat source at the sample surface (ref 8). However, the optical path lengths of the pump and probe beams, driving electronics, and photodetectors all introduce additional frequency-dependent phase shifts into the signal, which is collectively written as $\varphi_{ext}$. The approach to account for this external phase shift is to split 1% of the pump beam with a beam sampler and temporarily direct it into the post-sample photodiode with a flip-mirror. $\varphi_{ext}$ is then recorded over the frequency range of the measurement and this quantity is subtracted from the measured phase signal before data fitting to the thermal model. The reference path length should be as close as possible to the total path length from the beam sampler to the sample surface plus the path length from the sample surface to the photodetector. This was achieved by temporarily replacing the dichroic mirror that combines the pump and probe beams with a mirror that allowed a significant fraction of the pump beam to reach the detector. The 785 nm filters were removed, and the phase signal from the leakage beam and the sampled beam were compared. A translation stage is used to adjust the sampled path until the measured phases agree to within 0.01° at 20 MHz, corresponding to a path length difference of ~40 µm.

Figure 2:
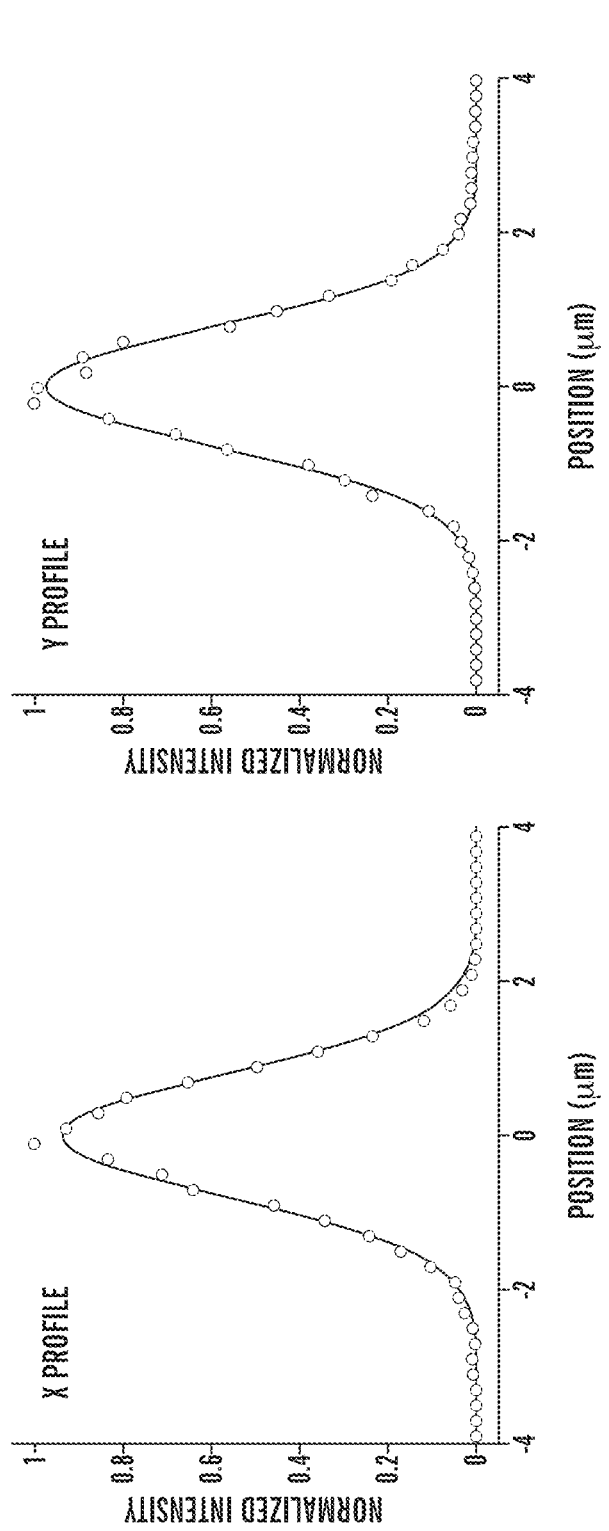
FIG. 2 is a set of plots showing knife edge measurement of the focused probe spot in x and y directions. The $1/e^2$ radius is 1.6 µm in the x direction and 1.6 µm in they direction.

At frequencies below 10 MHz, the laser spot size is one of the primary sources of experimental uncertainty in FDTR measurements (ref 8, 10). A two-dimensional knife-edge technique was used to measure both pump and probe laser spot sizes. A glass slide coated with 100 nm of gold is patterned with a square transparent window, and the transmitted light is measured with photodetector as the sample is scanned in two dimensions. The spatial derivative of the signal is fit with a Gaussian profile in both the x and y directions, with a typical repeatability of ±0.05 µm. FIG. 2 shows an example of the probe spot profile with a 10× objective, where the 1/e2 radius is 1.6 µm in the x and y directions. A CCD camera was used to focus on the knife edge before spot size measurement. During measurement of actual samples, the height of the sample is adjusted until the CCD image is in sharp focus, ensuring that the sample plane is at the same location where the spot profiles were measured.

The sample must remain within the depth of focus of the objective lens over the scan range (80×80 µm in this case) to avoid defocusing of the laser spots enough to affect the measurement. Taking a typical tolerance of w=1.05$w_0$, where w is the spot radius and $w_0$ is the minimum focused radius, the depth of focus can be determined using Gaussian beam optics: $\Delta z = \pm 0.32 \pi w_0^2/\lambda$ where $\lambda$ is the wavelength, and the minimum spot radius is determined by $w_0 = 0.61\lambda/$NA where NA is the numerical aperture of the objective lens (ref 19). For the 10× objective (NA=0.25) at the probe wavelength of 532 nm, this yields a depth of focus of $\Delta z = \pm 3.18$ µm, and for the 20× objective (NA=0.4), $\Delta z = \pm 1.24$ µm. Practically, the flatness of the sample stage was checked with a reference sample sensitive to radial conduction (and therefore spot size), such as a metal film on a glass substrate, taking measurements at the four corners of the reference sample to ensure that the sample plane is sufficiently parallel to give consistent results at each location.

Signal Analysis

Figure 3:
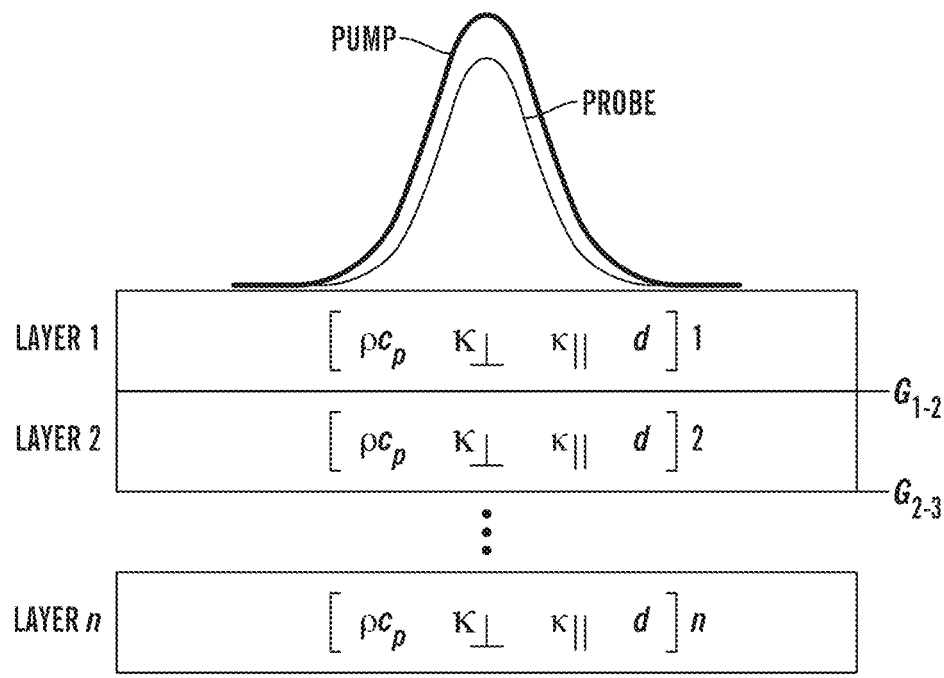
FIG. 3 is a diagram of multilayer sample with Gaussian pump and probe spots. For each layer the volumetric heat capacity, $C=\rho c_p$, the cross-plane and in-plane thermal conductivities, $k_\perp$ and $k_\parallel$, the layer thickness, d, and the thermal interface conductance to the next layer, G, are included.

The measurement of thermal properties is done as an inverse problem, minimizing the difference between the observed and calculated phase lag at different frequencies by adjusting parameters of interest in a thermal model. The model, described in detail in Ref 8, gives the frequency response of the sample surface temperature in response to a Gaussian heat source on a multilayer stack of materials. A typical measurement configuration is shown in FIG. 3. Five physical parameters was used for each layer in the sample: the volumetric heat capacity, $C=\rho c_p$, the cross-plane and in-plane thermal conductivities, $k_\perp$ and $k_\parallel$, the layer thickness, d, and the thermal interface conductance to the next layer, G. Thus for an n-layer sample, there are 5n−1 physical properties, of which 1-4 are typically determined in a given measurement. If the thickness of the bottom layer is greater than the penetration depth of the thermal wave at the lowest frequency, a semi-infinite boundary condition can be used for the final surface and the thickness of the bottom layer d can be made arbitrarily large. Otherwise, the actual thickness of the final layer must be used in the solution, and the boundary condition at the bottom surface can be taken as adiabatic, isothermal, or convective, depending on how the sample is mounted. The thermal penetration can be estimated from $\delta_t = \sqrt{2\alpha/\omega_0}$, where $\omega_0$ is the lowest frequency and $\alpha$ is the thermal diffusivity of the bottom layer. A more accurate estimation for the minimum semi-infinite thickness that accounts for heat flow in all the layers can be obtained by assuming a finite thickness $d_n$ for the bottom layer and plotting the phase at $\omega_0$ as a function of $d_n$. For all the samples described herein, the total thickness was at least 500 µm and the results are insensitive to the backside boundary condition.

The optical power impinging on the sample from the modulated pump beam at frequency $\omega$ is given by $Q_{modulation}=(\frac{1}{2})Q_{pump}(1+\cos \omega t)$ where $Q_{pump}$ is the maximum DC output power of the pump laser. The lock-in amplifier detects the amplitude and phase of the harmonic component of the probe signal at $\omega$. The amplitude of the lock-in voltage is given by $$|V_{LI}| = \frac{1}{2} Q_{pump} Q_{probe}(1-R_{\lambda pump})\left(\frac{dR}{dT_{\lambda probe}}\right) G_{det}|H(w)|, \quad (1)$$

where $Q_{probe}$ is the probe power that is impinging on the sample surface, $R_{\lambda pump}$ is surface reflectivity at the pump wavelength, $$\frac{dR}{dT_{\lambda probe}}$$

is the thermoreflectance coefficient at the probe wavelength, and $G_{det}$ is the product of the trans-impedance amplifier gain and the photodiode responsivity at the probe wavelength. H($\omega$) is a complex number that represents the frequency response of the sample surface temperature to a periodic heat flux, weighted by the intensity distribution of the probe beam. An explicit expression for H($\omega$) for a multilayer geometry such as the one shown in FIG. 3 can be found in Ref 8, although in general any linear transfer function for the thermal response can be used. The phase measured by the lock-in amplifier is given by $$\phi_{LI} = \tan^{-1}\frac{\Im(H(\omega))}{\Re(H(\omega))} + \phi_{ext}, \quad (2)$$

where $\varphi_{ext}$ is the net external phase introduced by the optical paths and electronic components. The measured $\varphi_{ext}$ is subtracted at each frequency before fitting the lock-in phase data with the model for $H(\omega)$.

Figure 4:
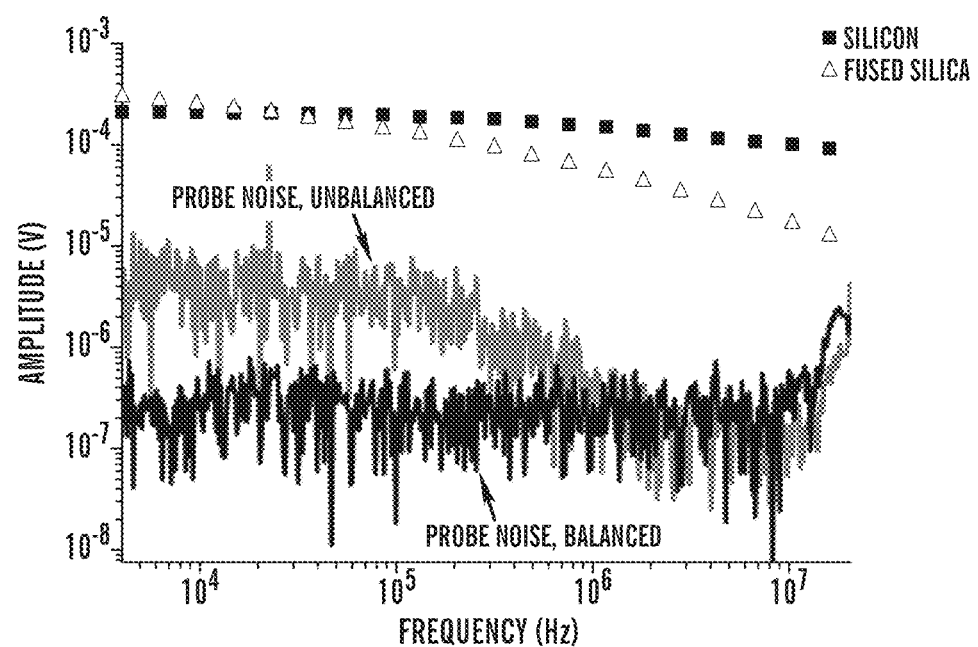
FIG. 4 is a plot showing measured data for silicon and fused silica coated with 64 nm of gold, compared with the system noise floor for the balanced and unbalanced detection scheme. With the balanced scheme, the signal to noise ratio is increased at low frequencies by more than an order of magnitude. At frequencies above 10 MHz, coherent RF pickup by the detector and signal cables is the dominant source of noise.

In FIG. 4 the noise floor of the system described herein under typical experimental conditions with a lock-in amplifier bandwidth of 3.4 Hz and a Thorlabs PDB410A detector ($G_{det}$=7.5×10$^3$ V/W at 532 nm) is shown, along with measured data for a sample with high thermal conductivity (silicon, κ=148 W/m K at 300 K) and low thermal conductivity (fused silica, κ=1.33 W/m K at 300 K), coated with 64 nm of gold. The noise floor was measured by blocking the pump beam while still sending the lock-in reference signal to the laser diode driver. The noise was measured in both balanced and unbalanced configurations, and it shows that the balanced detection scheme reduces the noise inherent in the probe beam by more than an order of magnitude for frequencies below 1 MHz. At frequencies above 10 MHz, radio-frequency noise picked up by the detector and signal cables becomes the dominant source of noise. For the measured data, 8.0 μm and 1.6 μm are used for the pump and probe 1/e$^2$ radii, respectively, and the power in the pump and probe beams was chosen to limit the steady temperature rise in the sample to approximately 2 K for the silicon sample and 5 K for the fused silica sample. The steady temperature rise was calculated by taking the low frequency limit of $H(\omega)$ multiplied by the absorbed pump and probe powers, using 3% for the absorption of gold at 785 nm and 20% at 532 nm. For samples with low thermal conductivity, the steady temperature rise is a limiting factor for the signal to noise ratio.

Imaging with FDTR

Figure 5:
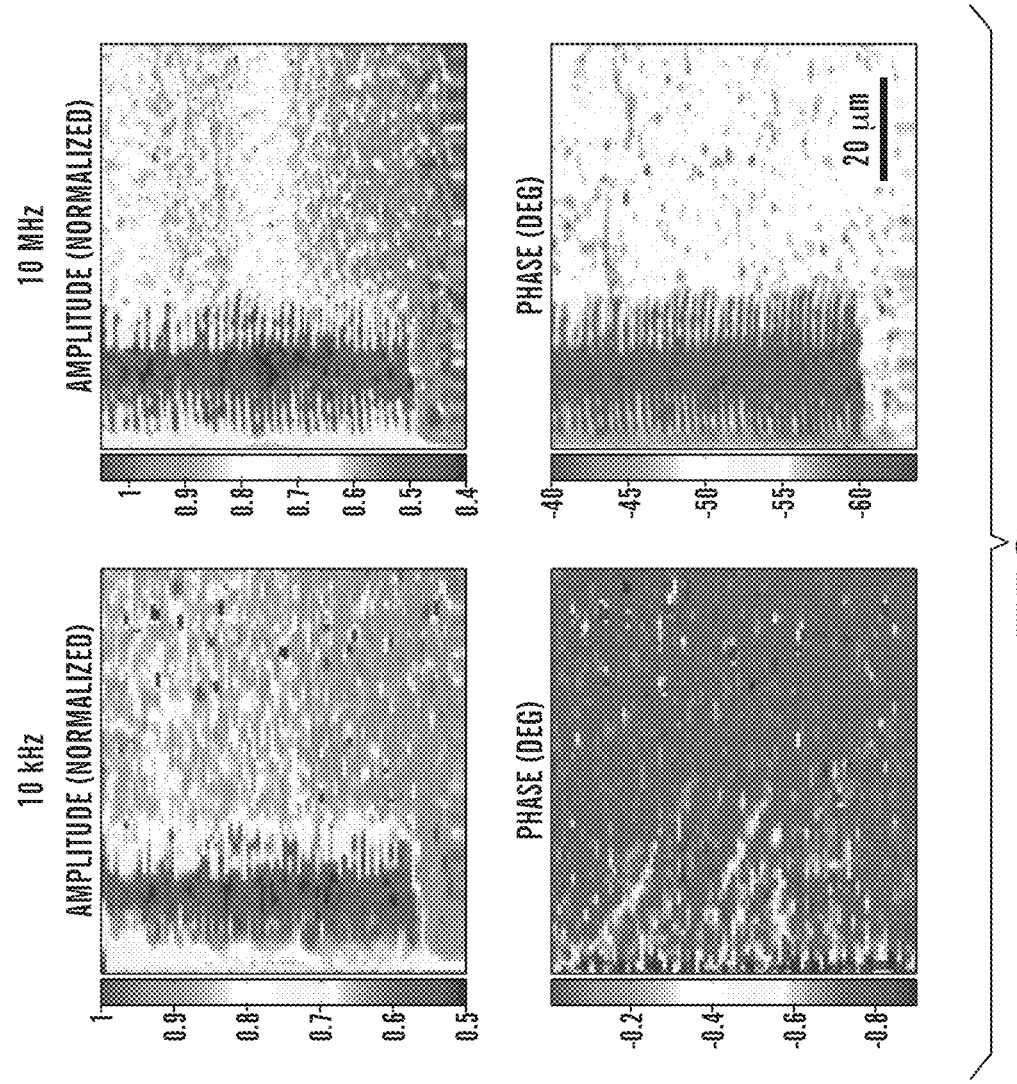
FIG. 5 is a set of amplitude and phase images of a metal film on a silicon substrate at 10 kHz (left column) and 10 MHz (right column).

Images are obtained by scanning the sample stage in two dimensions while recording amplitude and phase data from the lock-in amplifier at up to six frequencies simultaneously. At every frequency both an amplitude and a phase image are obtained. In FIG. 5, amplitude and phase images at 10 kHz and 10 MHz are shown for a 300 nm metal film on a silicon substrate. A vertical scratch on the left half of the image penetrates to the substrate, while fine horizontal cracks extend laterally outward from the scratch. The amplitude image is sensitive to the overall reflectivity of the sample, and looks similar at both frequencies because the metal film reflects significantly more of the probe beam than the underlying substrate. The phase image, however, is dramatically different because the phase data are governed by heat transfer in the sample and is independent of the absolute magnitude of the reflectivity. At 10 kHz, the thermal signal is dominated by the response of the substrate and the 300 nm film is invisible, while at 10 MHz, where thermal wavelength is approximately 30 times shorter, the phase image reveals cracks and other details in the film and is insensitive to the substrate. The amplitude image actually also depends on modulation frequency, because the magnitude of the lock-in voltage given by Eq. (1) does depend on the temperature oscillations, but this effect is masked by the much larger effect of the absolute variation in probe light reflected to the detector from the different regions of the sample.

A. Thermal Property Imaging

Phase images are obtained at multiple frequencies chosen for maximum sensitivity to various thermal properties, and then this set of phase images is converted into quantitative thermal property maps. During a single-point FDTR measurement, phase data are obtained for a wide range of modulation frequencies, and thermal properties of the sample are determined through multi-parameter fitting of the phase vs. frequency data to the calculated phase lag.

Depending on the number and types of layers in the sample, several combinations of the properties illustrated in FIG. 3 may be determined. Liu et al. have discussed in detail how different combinations of thermal properties such as thermal conductivity, volumetric heat capacity, and thermal interface conductance play a role in the thermal response in different frequency regimes (ref 12). The number of parameters that can be fit is maximized when the frequency range is sufficiently large such that the thermal penetration depth $L_p$ varies from being larger to smaller than the pump laser spot diameter, causing heat flow to transition from a two-dimensional, axisymmetric regime to a one-dimensional regime. In the former, the phase signal depends primarily on the quasi-isotropic thermal conductivity and is sensitive to in-plane transport, while at high frequency the phase is controlled by the thermal effusivity $\sqrt{\kappa C}$ and the thermal interface conductance of the surface layer. For a frequency range of 4 kHz-50 MHz, $L_p$ varies from 84 μm to 753 nm in silicon (thermal diffusivity=8.9×10$^{-5}$ m$^2$/s at 300 K) and from 8.2 μm to 73 nm in SiO$_2$ (thermal diffusivity=8.46×10$^{-7}$ m$^2$/s at 300 K), so for the majority of materials, spot diameters on the order of a few μm effectively cover the 1D-2D transition.

Some common imaging scenarios are considered and Eq. (2) is used to determine a set of imaging frequencies to map a desired set of thermal properties. In order to maximize imaging speed, the pump beam is simultaneously modulated with six sine waves and six phase images are recorded simultaneously. It is important to space these frequencies properly to reliably fit a desired set of thermal properties. The tool for this is the sensitivity function $S_x(\omega)$, which describes how a change in a parameter x in the thermal model affects the phase signal as a function of frequency. Rather than use a partial derivative of the phase with respect to a model parameter, here $S_x$ is defined as the phase difference caused by changing a parameter x by a certain tolerance such as ±10%: $S_{x,10\%}(\omega)=\varphi|_{1.1x}(\omega)-\varphi|_{0.9x}(\omega)$. In this work all sensitivities are calculated for a change in property value of ±10%. The reason for adopting this definition is that it gives a convenient way to determine in which frequency range it will be possible to fit a particular property to a certain tolerance by directly comparing the sensitivity to the phase noise floor.

Figure 6A:
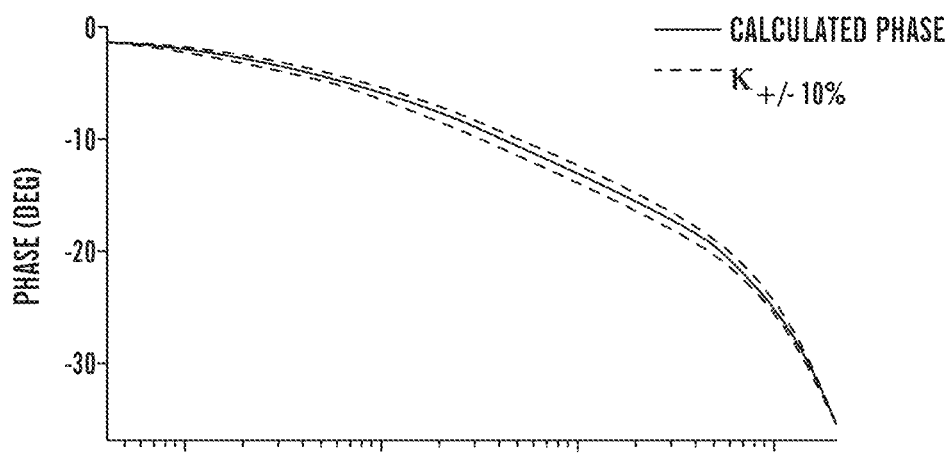
FIG. 6A is a plot showing calculated phase for 64 nm Au on a silicon substrate. Dashed lines show the effect of varying the thermal conductivity of silicon by ±10%.
Figure 6B:
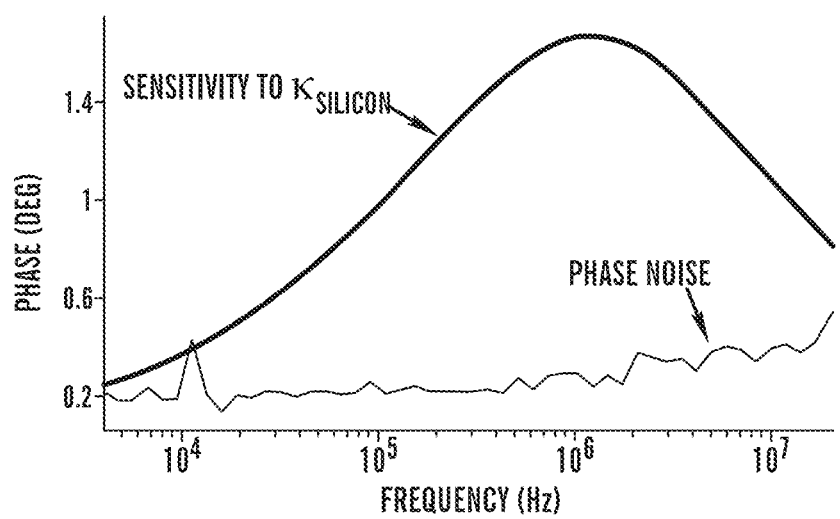
FIG. 6B is a plot showing the sensitivity to thermal conductivity, defined here as the difference of the two dashed lines shown in FIG. 6A, is plotted along with the standard deviation in signal phase that determines the minimum change in a parameter that can be resolved.
Figure 7A:
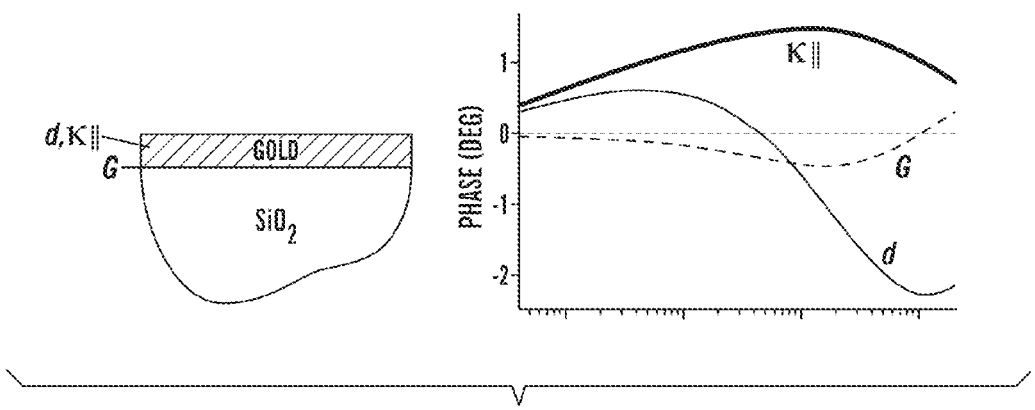
FIGS. 7A-7D shows sensitivity to different thermal properties for four configurations.
Figure 7B:
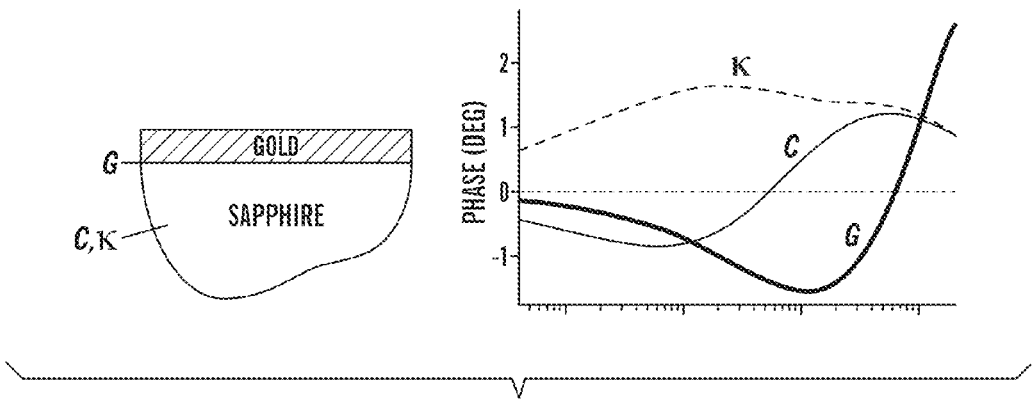
Figure 7C:
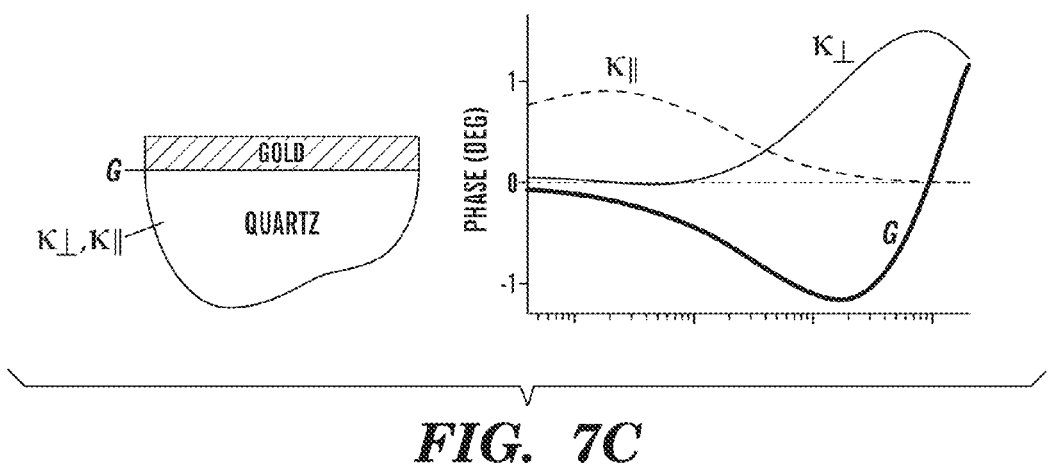
Figure 7D:
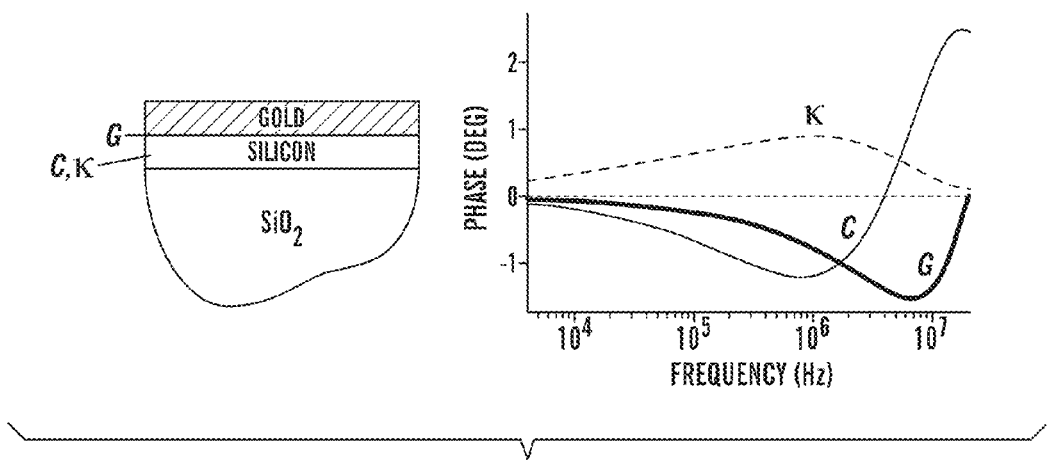

A sample sensitivity calculation is illustrated in FIG. 6 for a 64 nm Au film on a silicon substrate, with 8.0 μm and 1.6 μm 1/e$^2$ spot radii for the pump and probe beams, respectively. In FIG. 6A, the calculated signal is shown, along with the curves obtained by varying the thermal conductivity of the silicon substrate by ±10%. In FIG. 6B the sensitivity is plotted to thermal conductivity, which is obtained by taking the difference of the two bounding curves, and is compared to the plotted phase noise floor, which is determined from the standard deviation of 50 phase measurements at each frequency. In this example, the sensitivity is greater than the phase noise floor across the entire frequency range, and the signal will be most sensitive to thermal conductivity near 1 MHz.

In FIG. 7 four cases of thermal property characterization are shown, along with sensitivity curves for the properties of interest in each case. Imaging speed is optimized by collecting data for 2-6 frequencies simultaneously, using the sensitivity curves as a guide for choosing the frequencies to ensure one can reliably fit all the properties of interest. In FIG. 7A, mapping variations in the properties of a thin metallic film on a substrate is considered, where it is of interest in simultaneously determining the in-plane thermal conductivity (which can be used to determine an electrical conductivity map via the Wiedemann-Franz law (ref. 20)), film thickness, and the thermal interface conductance to the substrate. In FIG. 7B, the thermal conductivity, heat capacity, and interface conductance for an unknown substrate are mapped. In this case the properties of the metal film are required; typically for this case the film is characterized with a reference substrate co-deposited with the sample of interest. In FIG. 7C it is of interest to map both in-plane and cross-plane thermal conductivities of an anisotropic sample along, with thermal interface conductance, and in FIG. 7D it is of interest to map variations in either the in-plane or cross-plane thermal conductivity, heat capacity, and thermal interface conductance of a thin film on a known substrate.

In each case, the sensitivity to the various properties in the thermal model varies differently from low to high frequency. For example, in FIG. 7C considering sensitivity to in-plane and cross-plane thermal conductivity, sensitivity to cross-plane transport is dominant at high frequencies in the 1D regime and sensitivity to in-plane transport is dominant at low frequencies in the 2D regime. In order to reliably obtain quantitative maps of a set of properties from multi-parameter fitting, at least two frequency points are selected for each property in a range where sensitivity is largest. In addition, the sensitivity for many properties crosses the x-axis at particular frequencies, indicating the phase is insensitive to that particular property. These frequencies typically included in the set of six, since at these frequencies the number of fitting parameters is reduced by one.

B. Imaging of a Patterned Interface

Figure 8A:
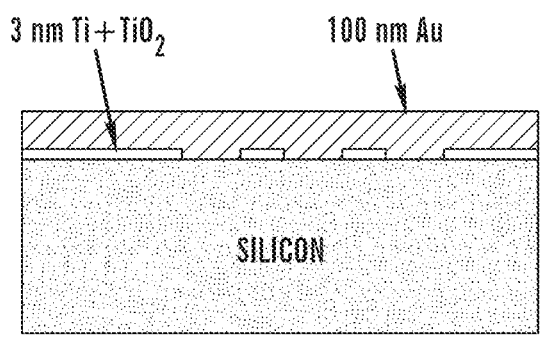
FIG. 8A is a diagram of the cross-section of the test sample, where a patterned, oxidized titanium thin film on a silicon substrate is coated with 100 nm of gold.
Figure 8B:
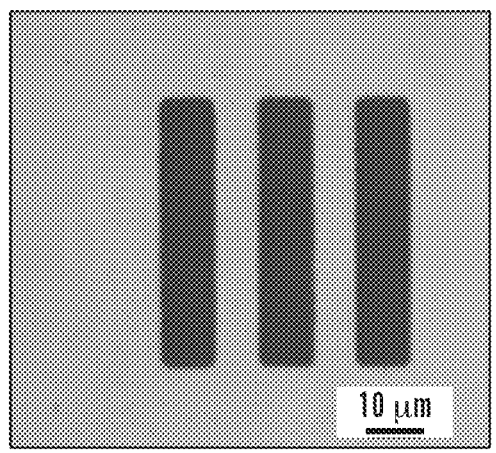
FIG. 8B is an optical image of the mask used for photolithography.

As a demonstration, a sample with a patterned variation in the thermal interface conductance, G, between a gold film and a silicon substrate is created. This was accomplished by patterning a 3 nm film of titanium on a silicon substrate using photolithography and a lift-off process. During this process, the patterned titanium film was exposed to air, allowing it to oxidize. Following lift-off, the entire sample was coated with a uniform film of gold 100 nm thick using electron beam deposition. The test sample is shown in FIG. 8. The thickness of the titanium layer is assumed to be the target deposition value of 3 nm, and the overall thickness and thermal conductivity of the gold/titanium layer were determined by FDTR measurement of a fused silica reference sample placed next to the patterned sample in the deposition chamber.

Figure 9B:
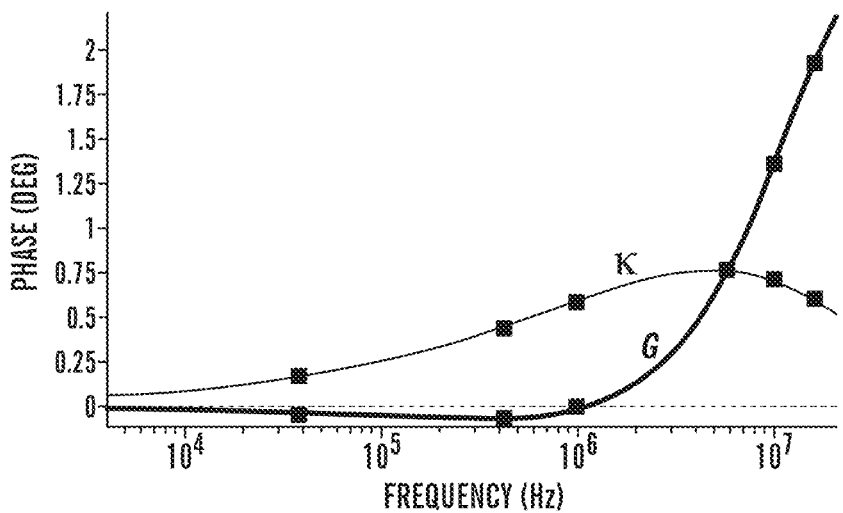
FIG. 9B is a plot showing the sensitivity to substrate thermal conductivity, κ, and thermal interface conductance, G, are used to choose the imaging frequencies.
Figure 10:
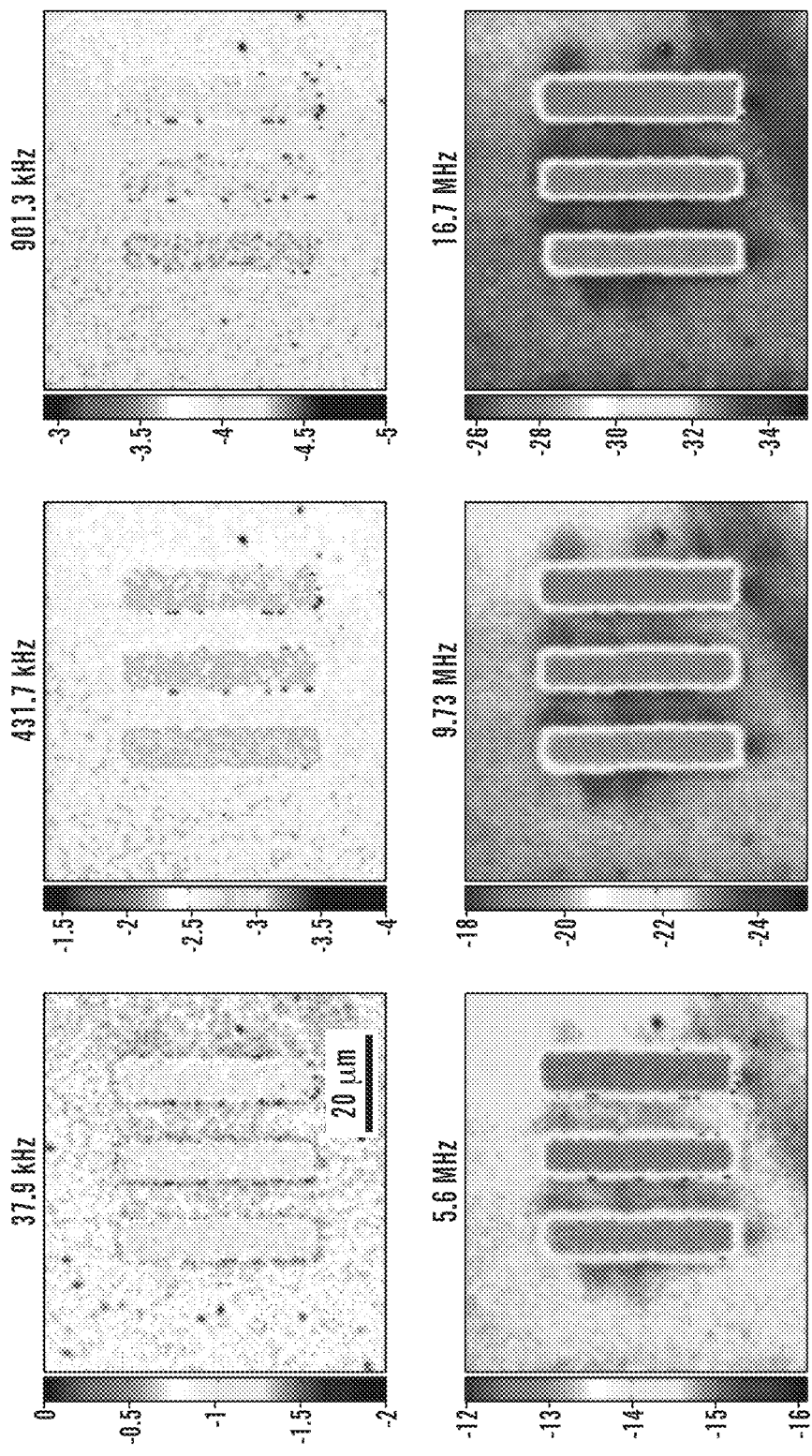
FIG. 10 is a set of phase images acquired at the six modulation frequencies shown in FIG. 9.

In FIG. 9A, a single point FDTR measurement of the sample in a region without titanium is plotted, along with the best model fit. Using the best fit values for the interface conductance and substrate thermal conductivity (38 MW/m$^2$K and 141 W/mK, respectively), the ±10% phase sensitivity for G and for the thermal conductivity of the substrate, κ, is plotted in FIG. 9B. Based on the sensitivity curves, six frequencies are selected to cover the range where the signal is sensitive to both G and κ, including 901.3 kHz, where sensitivity to C is near zero. FIG. 10 shows phase images acquired at these six frequencies with a 20× microscope objective (NA=0.4), which yielded 1.7 μm and 0.75 μm for the pump and probe radii, respectively. These images are 160×160 pixels with a pixel size of 0.5 μm. The image contrast from the patterned interface agrees well with the sensitivity curve for G: contrast is low at low frequencies, and as expected the pattern is almost invisible at 901.3 kHz, while above 1 MHz, where the sensitivity to G increases with frequency, the contrast increases with each higher frequency.

Figure 11A:
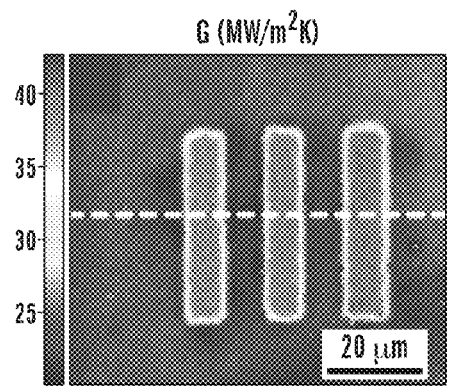
FIGS. 11A-11D show thermal property maps created from the six frequency images in FIG. 10, with a pixel size of 0.5 µm.
Figure 11B:
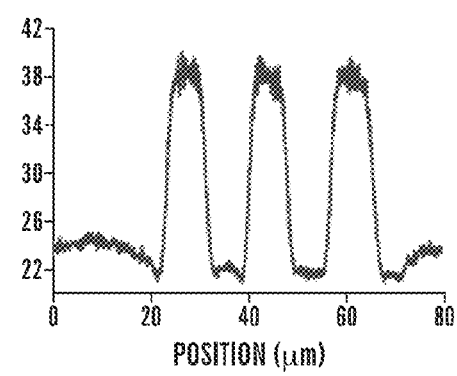
Figure 11C:
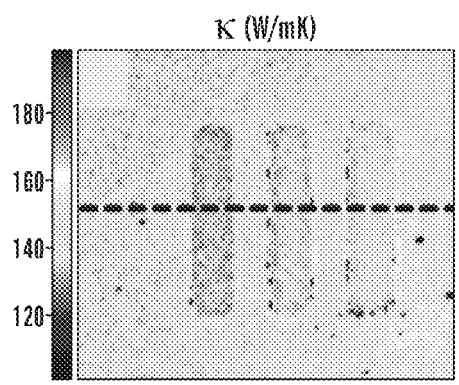
Figure 11D:
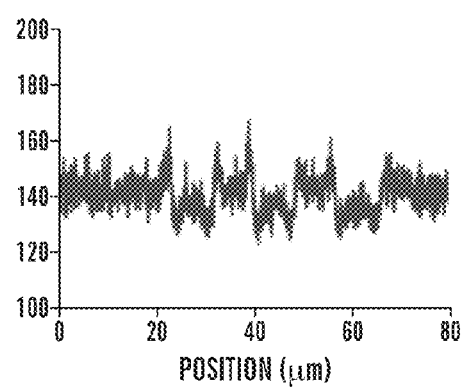

Using these six images, quantitative thermal property images for G are generated and by fitting the six phase data points at every pixel to the thermal model. These are shown in FIG. 11. The titanium pattern is clearly evident in FIG. 11A, while the substrate thermal conductivity map in FIG. 11C shows a relatively uniform image. The average value for G inside the stripes is 38 MW/m$^2$K, similar to reported values for gold on silicon where the native oxide on the silicon was not stripped prior to film deposition (ref 21). The G value outside the stripes, 22-24 MW/m$^2$K, is much less than typical Au/Ti/silicon interface conductances because of the oxide layer that was allowed to form before gold deposition. The low G value comes from the series thermal resistance of the Au/TiO$_2$ interface, the thermal conductivity of TiO$_2$/Ti layers, and the Ti/Si interface. The measured value of G close to the patterned stripes is lower than the value at the edge of the image (22 MW/m$^2$K vs. 24 MW/m$^2$K), and in the thermal conductivity image the outline of the Ti pattern is still visible. This is consistent with the presence of photoresist residue in the vicinity of the pattern that was not fully removed during the lift-off process, which would be expected to reduce interface conductance. The variations in the substrate thermal conductivity map, which are also on the order of 10%, are likely an artifact of data analysis with a thermal model that did not account for a residual photoresist layer.

The uncertainty in the FDTR images depends on the signal to noise ratio and on the uncertainty in the known parameters of the thermal model. The RMS phase noise of 0.2-0.4 degrees limits the minimum change in interface conductance that can be resolved to roughly ±2% and the minimum change in substrate conductivity to ±5%. However, in FDTR uncertainty due to modeling parameters, particularly the laser spot size and metal film properties, leads to a significantly larger overall uncertainty. This can be calculated using a procedure described by Malen et al. and for bulk samples gives an uncertainty of 10-15% (ref 10).

The images in FIG. 10 took 50 minutes to acquire as a set, with a measurement time per pixel of 0.12 sec. The measurement time is ultimately limited by the lock-in time constant at the lowest imaging frequency. At 40 kHz this could be significantly less than 1 ms and still provide a reasonable signal to noise ratio, but limitations of the data acquisition software require the use of a much longer time. Using optimized software and a fast scanning stage, imaging time for a 160×160 image could be reduced to tens of seconds. Likewise, converting the phase images to property maps took roughly 40 minutes on a PC with a 2 GHz CPU, where the data processing time per pixel was on the order of 0.1 sec for a 2-3 parameter fit of six frequencies. The fitting code is written in MATLAB and could be 1-2 orders of magnitude faster if implemented in a compiled language such as C.

Figure 12A:
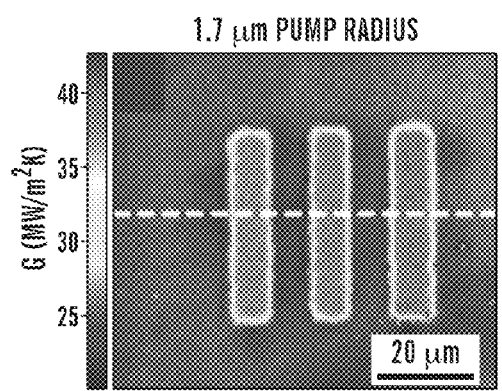
FIGS. 12A-12D show the effect of pump spot size on lateral resolution.
Figure 12B:
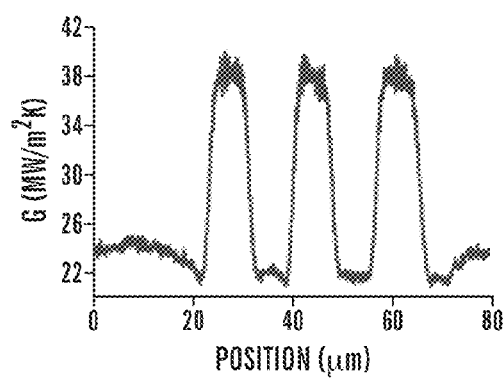
Figure 12C:
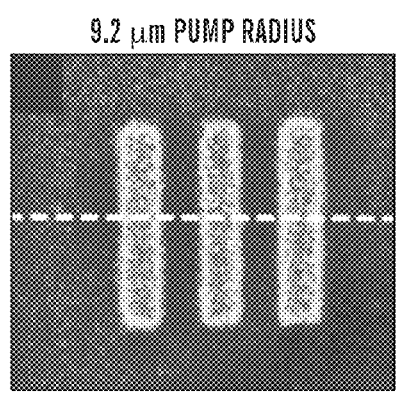
Figure 12D:
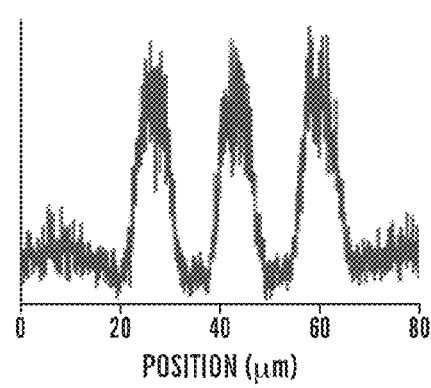

The minimum pixel size of FDTR imaging is determined by the extent of the region that is sampled during an FDTR property measurement at a point. Giving a simple set of resolution criteria is not straightforward because the heat flow under the pump and probe spots is affected by both the local thermal properties and the heating frequencies involved, making the effective resolution sample dependent. The thermal model used to analyze each pixel's data assumes that the properties are laterally uniform in the area under the pump and probe spots. Under this assumption, the sampling area for thermal properties is determined by both the effective radius of the periodic heat source and the probe intensity profile, which produces a signal that is the weighted average of the surface temperature field under the probe spot. The effect of the size of the heat source on resolution is illustrated in FIG. 12, where maps of thermal interface conductance from the test sample obtained with two different pump sizes are compared. In FIG. 12A, the pump radius is 1.7 µm, while in FIG. 12C, the pump radius is 9.2 µm. In both cases the probe radius was 0.75 µm. In some cases, sensitivity to certain parameters is enhanced with a larger pump spot, resulting in a tradeoff between numerical accuracy for property values and spatial resolution. The 5.4× larger pump spot also causes a much smaller temperature rise and thus a weaker signal, accounting for the higher noise level in the second image. For an isotropic bulk sample, the extent of the heat source around the pump spot can be estimated with the thermal/penetration depth, $\delta t = \sqrt{2\alpha/\omega 0}$ where $\omega_0$ is the lowest frequency and $\alpha$ is the effective thermal diffusivity. In more complex cases, such as multilayer stacks of different materials, or samples with significantly different in-plane and cross-plane thermal conductivities, an upper bound on sampled region can be determined using the largest diffusivity and the lowest imaging frequency.

Thermal property microscopy based on FDTR is presented herein. In particular embodiments, described herein is an FDTR microscope based on cw lasers that incorporates balanced photodetection to give a large signal-to-noise ratio for frequencies from 4 kHz to 20 MHz, and the methodology for imaging several combinations of thermal properties for a range of sample types. An exact analytical model for diffusive heat flow in a multilayer sample was applied, including radial heat transfer and the effect of finite laser spot sizes. Using this model, the sensitivity of the thermal phase signal to various properties was computed as a function of modulation frequency. The sensitivities are used to select a set of imaging frequencies that allow one to simultaneously fit multiple properties from a small number of images, which are acquired by scanning the sample while modulating the pump laser with multiple frequencies at once. In a non-limiting example, a silicon sample patterned with a thin layer of Ti was employed to demonstrate the technique, and maps of thermal interface conductance and substrate thermal conductivity were obtained by simultaneously fitting phase images acquired at six frequencies. The flexibility of this approach for quantitatively mapping many possible combinations of properties in layered structures makes it well suited to the analysis of microelectronic devices.

References for Example 1

1. D. G. Cahill, W. K. Ford, K. E. Goodson, G. D. Mahan, A. Majumdar, H. J. Maris, R. Merlin, and S. R. Phillpot, "Nanoscale thermal transport," Journal of Applied Physics, 93, 793 (2003), ISSN 00218979.
2. D. G. Cahill, K. Goodson, and A. Majumdar, "Thermometry and Thermal Transport in Micro/Nanoscale Solid-State Devices and Structures," Journal of Heat Transfer, 124, 223 (2002), ISSN 00221481.
3. O. Kwon, L. Shi, and A. Majumdar, "Scanning thermal wave microscopy (STWM)," Journal Of Heat Transfer-Transactions Of The Asme, 125, 156 (2003), ISSN 00221481.
4. D. G. Cahill, "Thermal conductivity measurement from 30 to 750 K: the 3ω method," Review of Scientific Instruments, 61, 802 (1990), ISSN 00346748.
5. C. A. Paddock and G. L. Eesley, "Transient thermoreflectance from thin metal films," Journal of Applied Physics, 60, 285 (1986), ISSN 00218979.
6. W. S. Capinski, H. J. Maris, T. Ruf, M. Cardona, K. Ploog, and D. S. Katzer, "Thermal-conductivity measurements of GaAs/AlAs superlattices using a picosecond optical pump-and-probe technique," Physical Review B, 59, 8105 (1999).
7. D. G. Cahill, "Analysis of heat flow in layered structures for time-domain thermoreflectance," Review of Scientific Instruments, 75, 5119 (2004), ISSN 00346748.
8. A. J. Schmidt, R. Cheaito, and M. Chiesa, "A frequency-domain thermoreflectance method for the characterization of thermal properties." The Review of scientific instruments, 80, 094901 (2009), ISSN 1089-7623.
9. J. Zhu, D. Tang, W. Wang, J. Liu, K. W. Holub, and R. Yang, "Ultrafast thermoreflectance techniques for measuring thermal conductivity and interface thermal conductance of thin films," Journal of Applied Physics, 108, 094315 (2010), ISSN 00218979.
10. J. A. Malen, K. Baheti, T. Tong, Y. Zhao, J. A. Hudgings, and A. Majumdar, "Optical Measurement of Thermal Conductivity Using Fiber Aligned Frequency Domain Thermore-flectance," Journal of Heat Transfer, 133, 081601 1 (2011), ISSN 00221481.
11. P. E. Hopkins, J. R. Serrano, L. M. Phinney, S. P. Kearney, T. W. Grasser, and C. T. Harris, "Criteria for Cross-Plane Dominated Thermal Transport in Multilayer Thin Film Systems During Modulated Laser Heating," Journal of Heat Transfer, 132, 081302 (2010), ISSN 00221481.
12. J. Liu, J. Zhu, M. Tian, X. Gu, A. Schmidt, and R. Yang, "Simultaneous measurement of thermal conductivity and heat capacity of bulk and thin film materials using frequency-dependent transient thermoreflectance method," Review of Scientific Instruments, 84, 034902 (2013), ISSN 00346748.
13. A. J. Schmidt, K. C. Collins, A. J. Minnich, and G. Chen, "Thermal conductance and phonon transmissivity of metal-graphite interfaces," Journal of Applied Physics, 107, 104907 1 (2010), ISSN 00218979.
14. A. Rosencwaig, "Thermal-wave imaging." Science (New York, N.Y.), 218, 223 (1982), ISSN 0036-8075.
15. S. Huxtable, D. G. Cahill, V. Fauconnier, J. O. White, and J.-C. Zhao, "Thermal conductivity imaging at micrometer-scale resolution for combinatorial studies of materials." Nature materials, 3, 298 (2004), ISSN 1476-1122.
16. E. López-Honorato, C. Chiritescu, P. Xiao, D. G. Cahill, G. Marsh, and T. Abram, "Thermal conductivity mapping of pyrolytic carbon and silicon carbide coatings on simulated fuel particles by time-domain thermoreflectance," Journal of Nuclear Materials, 378, 35 (2008), ISSN 00223115.
17. B. Li, L. Pottier, J. P. Roger, D. Fournier, K. Watari, and K. Hirao, "Measuring the anisotropic thermal di usivity of silicon nitride grains by thermoreflectance microscopy," Journal of the European Ceramic Society, 19, 1631 (1999).
18. R. B. Wilson, B. a. Apgar, L. W. Martin, and D. G. Cahill, "Thermoreflectance of metal transducers for optical pump-probe studies of thermal properties." Optics express, 20, 28829 (2012), ISSN 1094-4087.
19. E. Hecht, Optics, 4th ed. (Addison-Wesley, San Francisco, 2002) ISBN 0-321-18878-0. 20N. W. Ashcroft and D. N. Mermin, Solid State Physics (Harcourt College, New York, 1976).
20. J. C. Duda, C.-Y. P. Yang, B. M. Foley, R. Cheaito, D. L. Medlin, R. E. Jones, and P. E. Hopkins, "Influence of interfacial properties on thermal transport at gold:silicon contacts," Applied Physics Letters, 102, 081902 (2013), ISSN 00036951.

Example 2: Thermal Conductance Imaging of Graphene Contacts

Suspended graphene has the highest measured thermal conductivity of any material at room temperature. However, when graphene is supported by a substrate or encased between two materials, basal-plane heat transfer is suppressed by phonon interactions at the interfaces. Frequency domain thermoreflectance is used to create thermal conductance maps of graphene contacts, obtaining simultaneous measurements of the basal-plane thermal conductivity and cross-plane thermal boundary conductance for 1-7 graphitic layers encased between titanium and silicon dioxide. The basal-plane thermal conductivity is found to be similar to that of graphene supported on silicon dioxide. The results have implications for heat transfer in two-dimensional material systems, and are relevant for applications such as graphene transistors and other nanoelectronic devices.

Frequency domain thermoreflectance (FDTR) imaging[13] of encased graphene is described, using thermal waves from 100 kHz to 50 MHz to image sub-surface graphitic multilayers and create micron-scale maps of the in-plane thermal conductance and TBC of two mechanically exfoliated graphene flakes encased between Ti and $SiO_2$. The obtained values indicate that depositing Ti has no significant impact on the thermal conductivity of graphene exfoliated on $SiO_2$.

Experimental

Figure 13A:
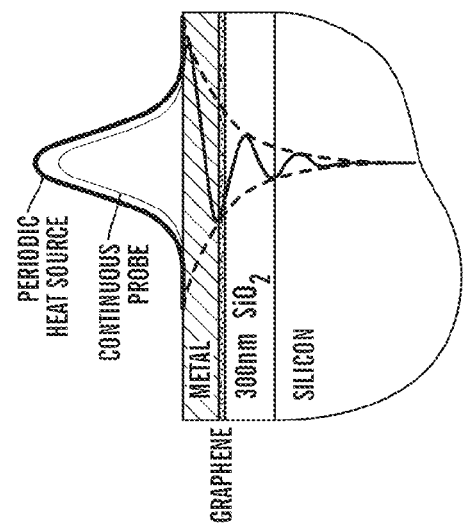
FIG. 13A is a diagram showing sample configuration of encased graphene flakes during FDTR imaging. The sample consists of four layers: a 50-100 nm metal coating, an exfoliated graphene flake, 300 nm of thermal $SiO_2$, and a p-type silicon substrate.

FIG. 13 shows a schematic of the sample configuration and experimental setup. Graphene flakes were encased between a metal layer and a thermally oxidized p-type silicon wafer. A periodically modulated continuous-wave laser (the pump beam) is focused to a Gaussian spot with a 1.6 μm $1/e^2$ diameter while a second, unmodulated laser beam was used to measure the surface temperature through a proportional change in reflectivity. The pump beam modulation frequency is varied and the phase lag of the probe signal is measured using a lock-in amplifier. Unknown thermal properties of the sample are extracted by minimizing the error between the phase data and an analytical solution to the heat diffusion equation. The multilayer diffusion model, described in Ref. 14, calculates the frequency response of the surface temperature to the pump beam, and includes cross-plane and radial transport as well as the TBC between each layer. Because the model is based on Fourier's law of heat conduction, the property values obtained are effective diffusion transport properties. The room temperature phonon mean free path (MFP) has been estimated with the 2D kinetic theory to be 775 nm for suspended single-layer graphene, and 10-50 nm for graphene encased between $SiO_2$.[9] Since this is significantly smaller than the pump laser spot diameter, a diffusive model is suitable.

Figure 14B:
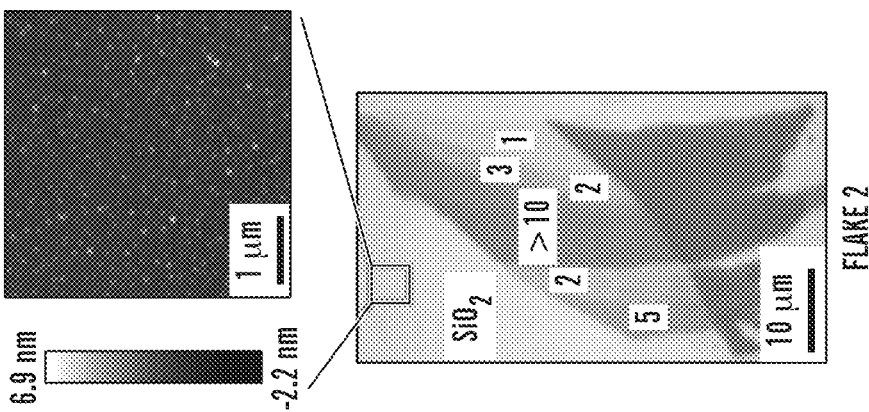
FIG. 14B is an optical image of graphene flake 2 together with an AFM image of the oxide region showing contaminant particles. The number of graphene layers is labeled on the flakes.
Figure 14A:
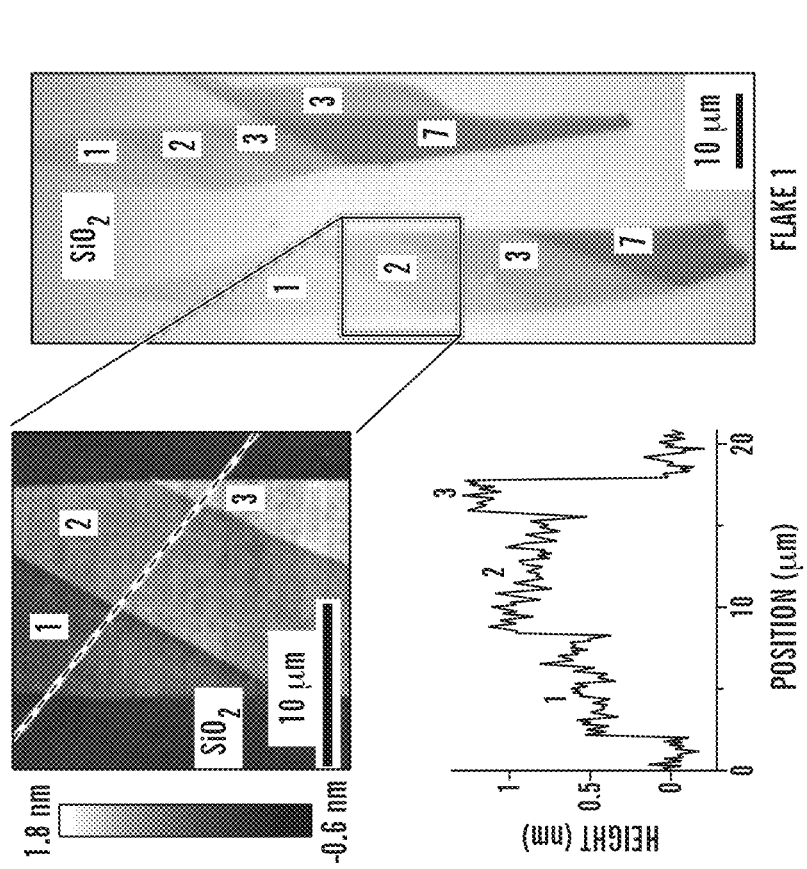
FIG. 14A is an optical image of graphene flake 1 together with an AFM image of the region indicated with a black box. The height profile along the dashed line shows one, two, and three layers of graphene sheets.

Two graphene samples were prepared by mechanical exfoliation of bulk graphite onto thermally oxidized p-type silicon substrates. The target thickness of the $SiO_2$ layer was chosen to be ~300 nm to maximize the contrast of graphene flakes under an optical microscope. After mechanical exfoliation, the two samples were annealed at 400° C. for 2 hours in forming gas to remove adhesive residue from the tape.[16] Optical images of the samples are shown in FIGS. 14A and 14B. The number of graphene layers within the flakes, labeled on each flake image, was determined by optical contrast and atomic force microscopy (AFM). For flake 1, the substrate was fresh. For flake 2, the substrate was used for mechanical exfoliation multiple times and between each exfoliation the substrate was cleaned with oxygen plasma ashing and piranha solution (sulfuric acid and hydrogen peroxide, 3:1). AFM images of the flake substrates showed similar surface roughness, but flake 2 had a significant amount of debris with a root mean square (RMS) roughness of ~1 nm, shown in the AFM image of FIG. 14B. After AFM characterization, a thin layer of metal was deposited with electron-beam evaporation. Flake 1 was coated with a 10 nm Ti adhesion layer followed by 46 nm of Au without breaking vacuum, while flake 2 was coated with 65 nm of Ti.

Results and Discussion

Thermal phase images were acquired by scanning the sample stage in two dimensions while recording phase data from the lock-in amplifier at six frequencies simultaneously. Maps of the in-plane thermal conductance, $G_\parallel$, and the TBC were created by performing a two-parameter fit of the diffusion model to the six phase data points at each pixel, after the properties of the other layers in the stack had been determined with additional measurements on reference samples. Here, flake 1 is used as an example to show the measurement procedure.

Figure 15A:
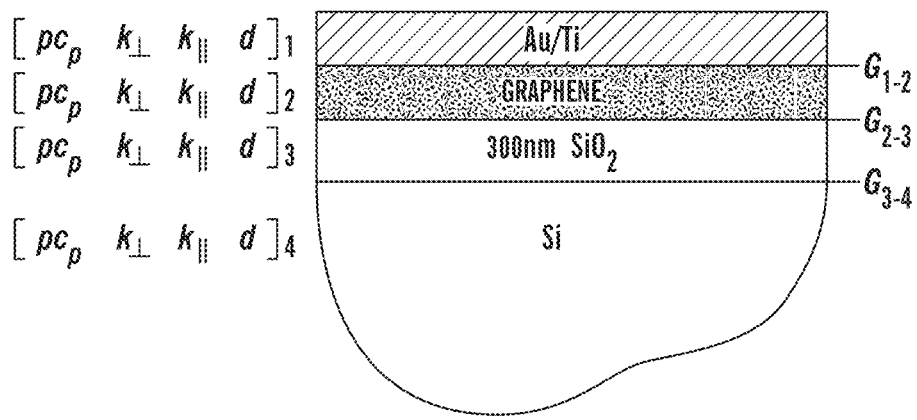
FIG. 15A is a diagram of sample configuration. Flake 1 consists of four layers: Au/Ti, graphene, 300 nm $SiO_2$, and p-type Si substrate. Each layer has five physical parameters: the volumetric heat capacity, $\rho c_p$, the cross-plane and in-plane thermal conductivities, $\kappa_\perp$ and $\kappa_\parallel$, the layer thickness, d, and the thermal boundary conductance (TBC) to the next layer, G.
Figure 15B:
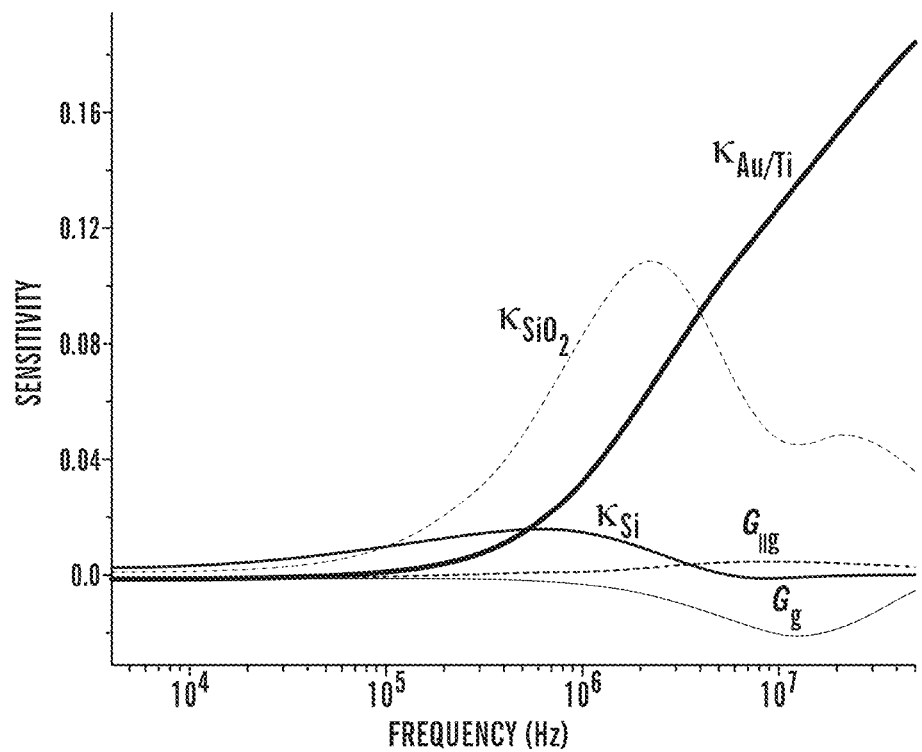
FIG. 15B is a plot of calculated sensitivity to the thermal conductivity of Au/Ti, $\kappa_{Au/Ti}$, the thermal conductivity of $SiO_2$, $\kappa_{SiO2}$, the thermal conductivity of silicon, $\kappa_{si}$, in-plane thermal conductance, and the TBC of graphene layer, $G_{\parallel,g}$ and $G_g$.

The configuration of flake 1, shown in FIG. 15A, includes four layers: Au/Ti, graphene, $SiO_2$, and p-type silicon. Graphene is treated as a layer with zero heat capacity, because the thermal time constant of the graphene layer is much shorter than the heating period in the measurements.[7] The interface between Au and Ti is neglected and they are treated as a single layer, since the TBC for metal-metal interfaces has been measured to be an order of magnitude higher than that for semiconductor and dielectric interfaces.[17] FIG. 15B shows the calculated sensitivity of the phase signal to $G_\parallel$ and the TBC of graphene layer and the next three most dominant parameters in the thermal model. The sensitivity to a property x was calculated from $\partial\varphi/\partial\ln x$, where φ is calculated with the thermal model using pump and probe spot radii of 0.8 μm and 0.7 μm, respectively.

To determine the thermal properties and thicknesses of all layers other than graphene, several reference samples of fused silica were co-deposited (thermal diffusivity=8.46× $10^{-7}$ $m^2$/s at 300 K, Ref 18), and pieces of the p-type silicon wafer with thermal oxide that was used for the graphene samples. The total thickness of Au/Ti on flake 1 is 62 nm, while the thickness of Ti on flake 3 is 65 nm, measured by AFM on reference glass slides. The oxidized p-type silicon wafer was purchased from University Wafer, Inc. The thickness of $SiO_2$ was measured to be 296 nm by ellipsometry. The K of the p-type silicon was measured by FDTR. The oxide was first etched away by immersing one piece of the substrate in buffered oxide etchant (BOE, 6:1) for 3 min. The substrate was left in air overnight and then coated with 74 nm of Au by electron-beam evaporation. The thermal conductivity was then measured to be 80 W $m^{-1}$ $K^{-1}$.

Because the metal thermal conductivity is an important parameter, several steps were taken to determine it as accurately as possible. The in-plane thermal conductivity, κ, and electrical conductivity, σ, of the Au/Ti film on the reference samples were first measured by FDTR with three spot sizes and a four-point probe, respectively. An effective Lorenz number was calculated using the Wiedemann-Franz law: $L=\kappa/\sigma T=2.43\times 10^{-8}$ $\Omega WK^{-2}$, where T is the absolute temperature.[19] This Lorenz number was then used to convert four-point probe electrical conductivity measurements from the oxide regions of flake 1 to a thermal conductivity of 140±4 W $m^{-1}$ $K^{-1}$, based on 23 measured values of σ.

Figure 16A:
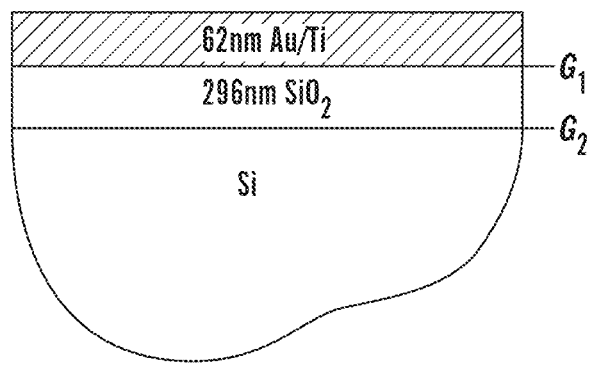
FIG. 16A is a diagram of sample configuration of the reference sample. Included are also the TBC between Au/Ti and $SiO_2$, $G_1$, and the TBC between $SiO_2$ and silicon, $G_2$.

The thermal conductivity of $SiO_2$ was measured by FDTR on a p-type silicon reference sample using the determined κ values of Au/Ti and p-type silicon. FIG. 16A shows the reference sample configuration. The κ of $SiO_2$ and the top and bottom TBCs, $G_1$ and $G_2$, contribute to the thermal resistance of the $SiO_2$ layer. Based on the reported thermal interface resistance values of thermally grown $SiO_2$ on silicon,[20] $G_2$ was taken to be 120 MW m$^{-2}$ K$^{-1}$. To separate κ of $SiO_2$ and $G_1$, FDTR was performed on the sample with three spot sizes using a 50× objective (NA=0.55), 10× objective (NA=0.25), and 4× objective (NA=0.1). The pump and probe spot radii were 0.8 μm and 0.7 μm, respectively, for the 50× objective, and 2.8 μm and 1.6 μm, respectively, for the 10× objective, while those for the 4× objective are 6.8 μm and 3.6 μm, respectively.

Figure 16B:
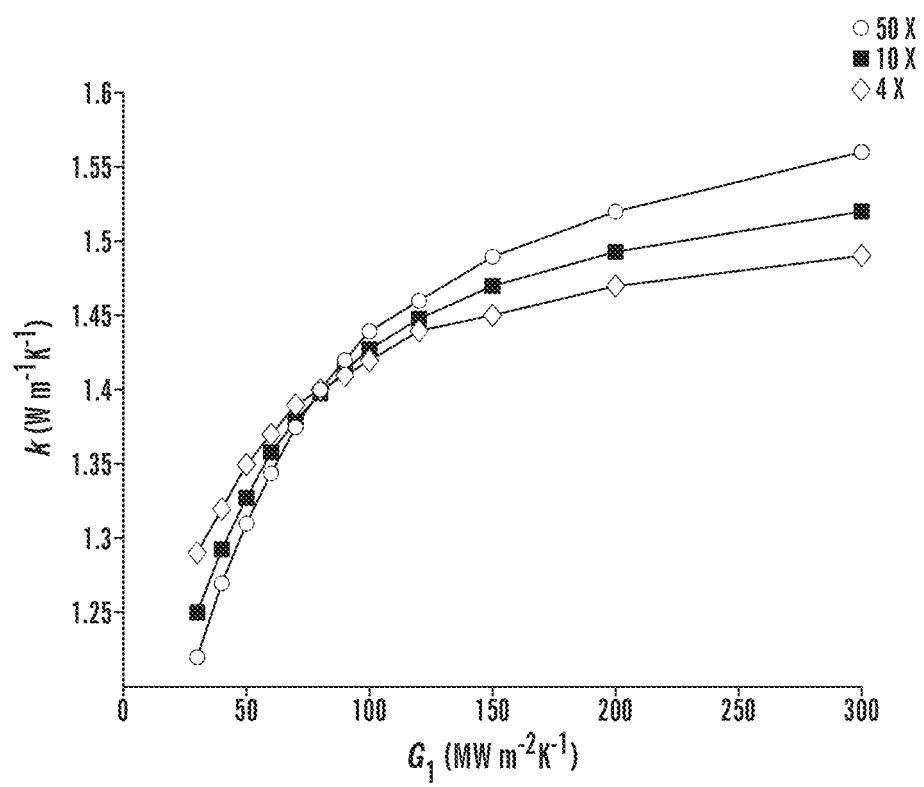
FIG. 16B is a plot of $\kappa$ of $SiO_2$ vs. $G_1$ measured with 50×, 10×, and 4× objectives.

By fitting the data from all three measurements simultaneously, there is sufficient sensitivity to determine both κ of $SiO_2$ and $G_1$. Alternatively, the data set at each spot size can be fitted with a series of κ–$G_1$ pairs obtained with single-parameter fitting. For any two spot sizes, only a single κ–$G_1$ pair will match both sets of data. This is shown in FIG. 16B, where $G_1$ was varied from 30 MW m$^{-2}$ K$^{-1}$ to 300 MW m$^{-2}$ K$^{-1}$ for data at three spot sizes and the corresponding κ values of $SiO_2$ were obtained by single-parameter fitting. The intersection gives κ=1.4 W m$^{-1}$ K$^{-1}$ for $SiO_2$ and $G_1$=80 MW m$^{-2}$K$^{-1}$. The κ value agrees to better than 3% with the reported value in Ref. 9 and $G_1$ is consistent with the measured value in Ref. 10.

The laser spot radii are also sensitive parameters in the thermal model. The effective spot radii are fitted to match phase data from the fully characterized reference samples. By using the piezo z-stage, the pump and probe spot radii could be repeatably focused to within 10 nm by maximizing the thermal signal. Values were similar to 2D knife-edge measurements but had ~5 times less variation. The fitted spot sizes, together with κ of the metal coating and all the other measured parameters, were then used to fit the graphene thermal conductance images. All the parameters for the graphene samples are summarized in Table I. The thermal conductivity of the 65 nm Ti on flake 2 was measured by FDTR directly on flake 2 in the regions without graphene, using the previously measured values of $SiO_2$ and silicon.

TABLE I

Fitting parameters for graphene samples.

| Material | $pc_p$ (10$^6$ J m$^{-3}$ K$^{-1}$) | k (W m$^{-1}$ K$^{-1}$) | d (nm) |
|---|---|---|---|
| Au/Ti | 2.49 (Ref. 18) | 140 ± 4 | 62 |
| Ti | 2.38 (Ref. 18) | 5.8 ± 0.4 | 65 |
| $SiO_2$ | 1.63 (Ref. 18) | 1.4 | 296 |
| P-type silicon | 1.65 (Ref. 18) | 80 | 5 × 10$^5$ |

Figure 17B:
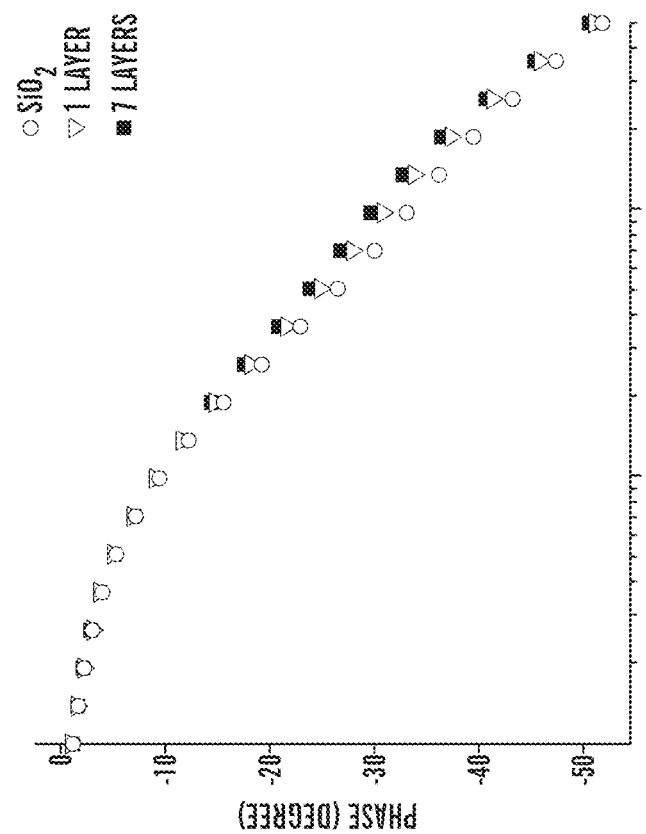
FIG. 17B is a plot of FDTR data acquired after metal coating from the three regions of flake 1 indicated in FIG. 17A: $SiO_2$ substrate, single-layer graphene and seven-layer graphene.
Figure 17A:
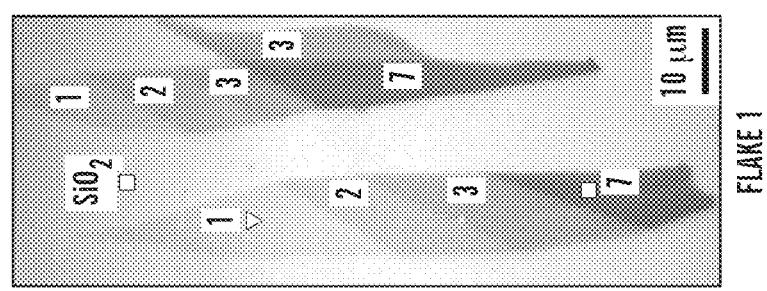
FIG. 17A is an optical image of flake 1.

In order to analyze the sensitivity of the measurement to the graphene layer, single-point FDTR measurements were performed using 20 frequencies at several locations on the flakes. The microscope objective was 50× with pump and probe 1/e$^2$ spot radii of 0.8 μm and 0.7 μm, respectively. In FIG. 17B, the phase data acquired from three regions on flake 1 are plotted: the $SiO_2$ substrate without graphene, single-layer graphene, and seven-layer graphene. To highlight the differences between the three sets of data, the difference between substrate and single-layer graphene data, and the difference between single-layer and seven-layer graphene data, are plotted in FIG. 17C. The phase difference at each frequency between different regions can be represented as $$\sum_{i=1}^{N} \frac{\partial \phi(\omega)}{\partial x_i} \Delta x_i,$$

where $\Delta x_i$ is the change in property $x_i$ and N is the total number of parameters in the thermal model. When there is a dominant change in one thermal property within the sample, the shape of difference data will match the phase sensitivity to that property. In FIG. 17E, the calculated phase sensitivity is plotted to the in-plane graphene conductance and to the cross-plane graphene conductance. The close agreement between the shapes of the curves in FIGS. 17C and 17E shows that the change in signal from single-layer graphene to the substrate is primarily from the change in cross-plane conductance, while the change from single-layer to seven-layer graphene is mainly due to the in-plane conductance, consistent with previous cross-plane measurements that showed a minimal change due to additional graphene layers.[10]

Figure 17D:
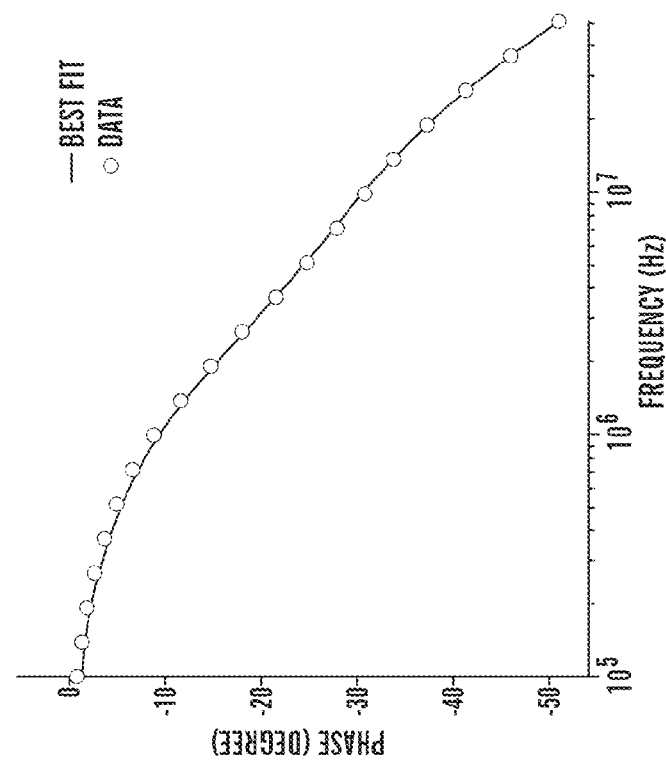
FIG. 17D is a plot of phase data of single-layer graphene from FIG. 17B and typical best fit of the thermal model.
Figure 17C:
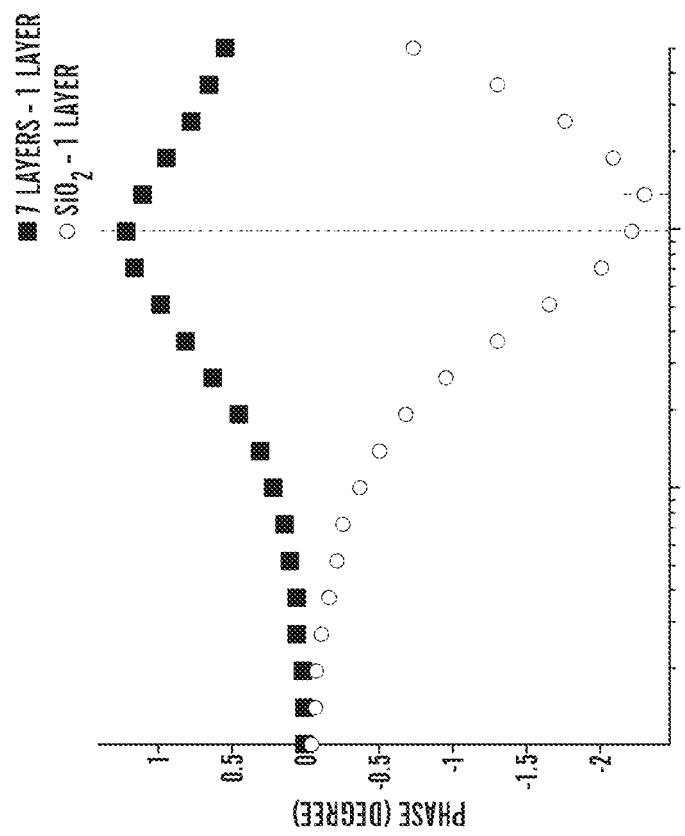
FIG. 17C is a plot showing difference between phase data from single-layer and seven-layer graphene (squares), and between single-layer graphene and the $SiO_2$ substrate (circles).
Figure 17E:
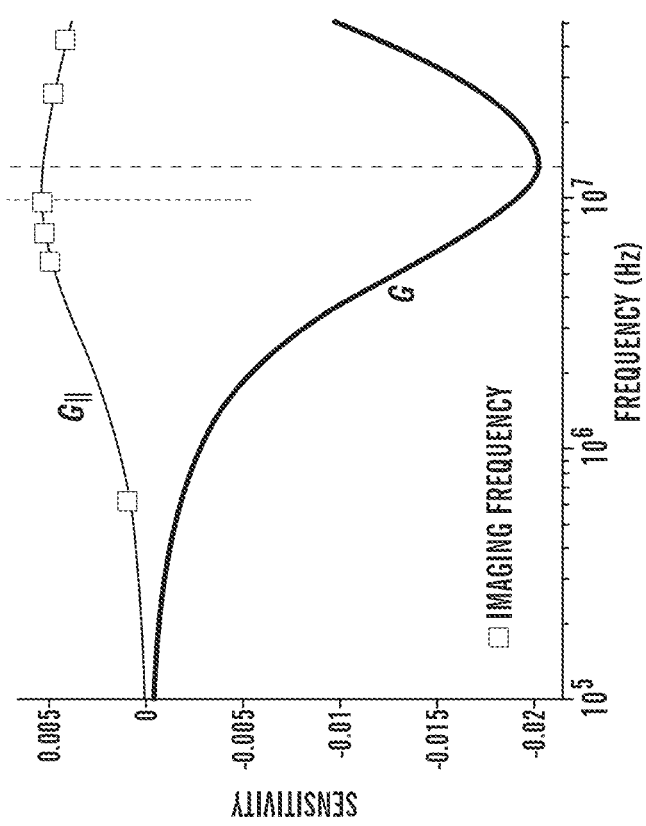
FIG. 17E is a plot of calculated phase sensitivity to graphene in-plane thermal conductance, $G_\parallel$, and to the TBC, G, of the Au/Ti/graphene/$SiO_2$ interface. The six frequency points used for imaging are shown as squares.

FIG. 17D shows a typical best fit of the model to a region of single-layer graphene, where nonlinear least squares minimization was used to simultaneously determine the thermal conductivity to be 617 W m$^{-1}$ K$^{-1}$ for single-layer graphene (assuming a thickness of 0.35 nm for a mono-layer of graphene[21]) and the TBC to be 22 MW m$^{-2}$ K$^{-1}$ for the Au/Ti/single-layer graphene/$SiO_2$ interface.

Figure 18:
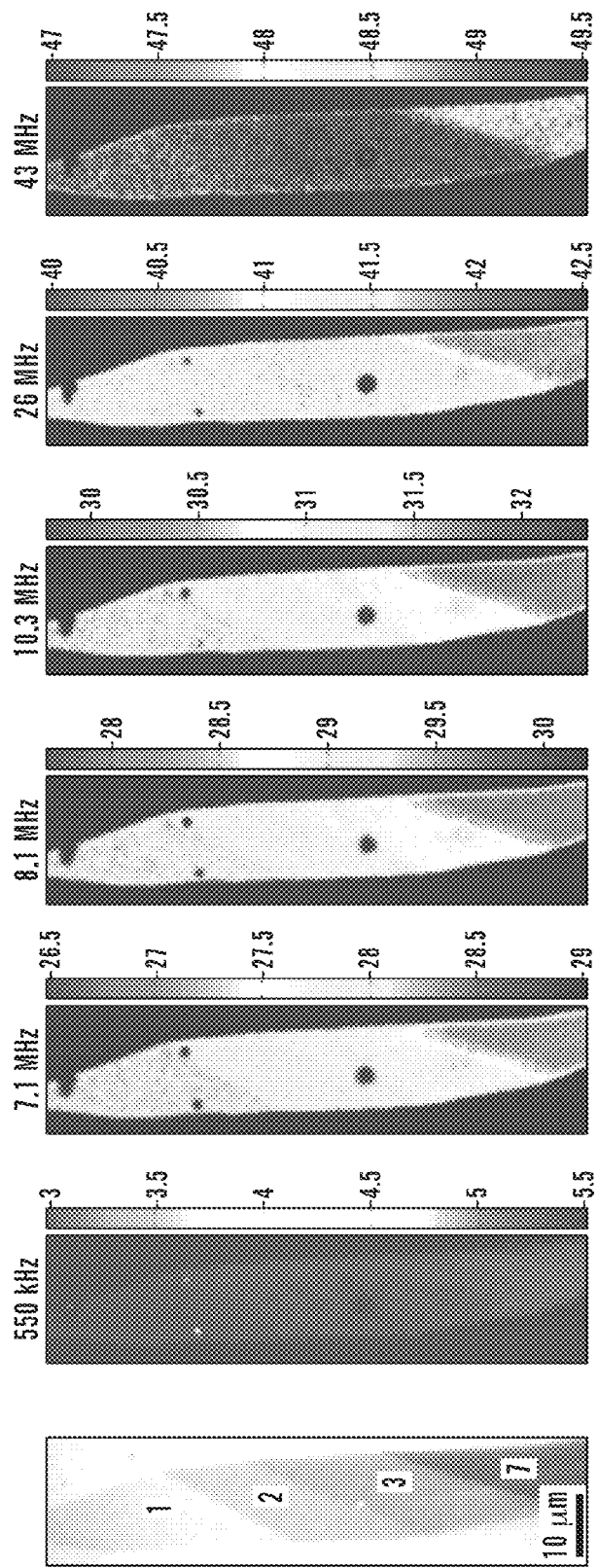
FIG. 18 is a set of phase images of flake 1 acquired simultaneously at six frequencies: 550 kHz, 7.1 MHz, 8.1 MHz, 10.3 MHz, 26 MHz, and 43 MHz. The image contrast between the layers follows the sensitivity to $G_\parallel$ shown in FIG. 17E.

To generate thermal property maps, phase images at six frequencies were simultaneously acquired for each graphene sample, selected based on the sensitivity to $G_\parallel$ as shown in FIG. 17E. FIG. 18 shows the six phase images taken for one portion of flake 1. The trend of image contrast between graphene layers agrees well with the calculated sensitivity to $G_\parallel$: contrast is low at the lowest frequency, arrives at a peak at 10.3 MHz, then decreases at the highest frequency.

Figure 19C:
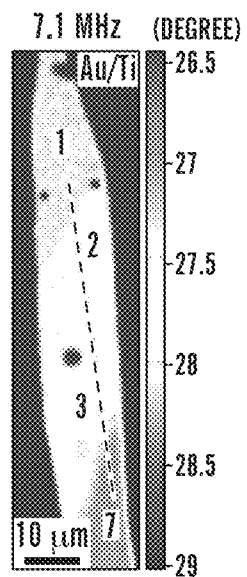
Figure 19C:
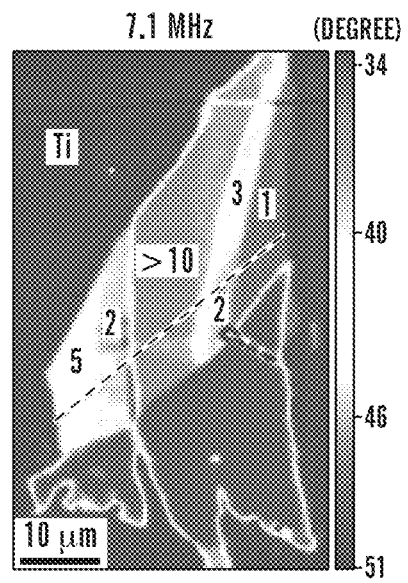
Figure 19C:
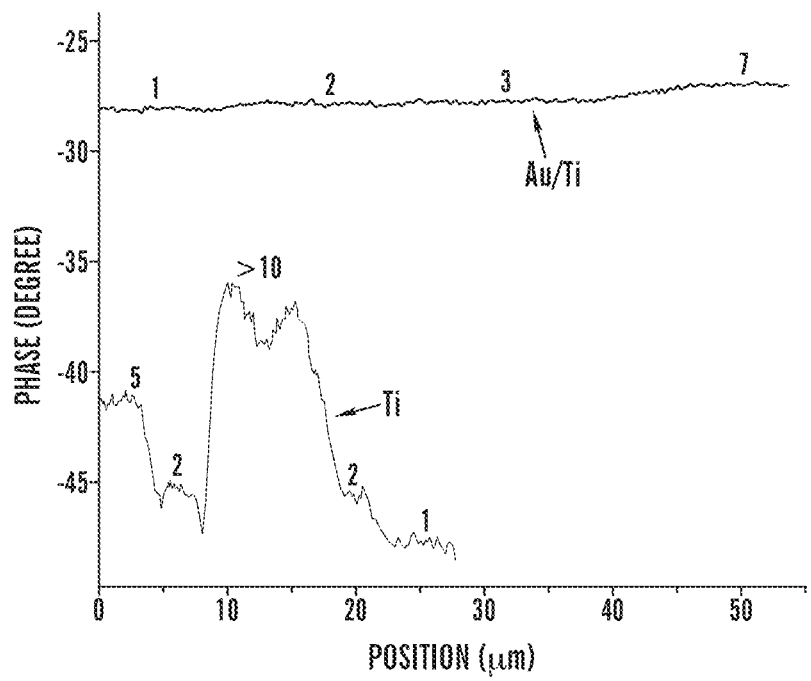

Although the different layers are quite clear in FIG. 18, the difference between the highest and lowest phase in each image is only 2.5°. To explain the small phase difference between layers, heat transfer in the substrate is temporarily neglected and in-plane heat transfer in the metal film and graphene is approximated with a one-dimensional thermal resistance network composed of two parallel elements R=(κd)$^{-1}$, where κ is the in-plane thermal conductivity and d is the thickness of the layer. Putting in the measured numbers for the Au/Ti film (d=62 nm, κ=140 W m$^{-1}$ K$^{-1}$) and the reported values for single-layer graphene on $SiO_2$ (d=0.35 nm, κ=600 W m$^{-1}$K$^{-1}$, Ref 8), only 2.4% of the heat is conducted through the graphene, while the remainder is conducted through the Au/Ti film. To enhance the heat flow in the graphene layer, and consequently decrease the experimental uncertainty, flake 2 was coated with 65 nm of Ti. The Ti film had a thermal conductivity of 5.8 W m$^{-1}$ K$^{-1}$, as shown in Table I. Repeating the calculation with the Ti values, the percentage of heat conducted in the graphene layer was found to increase to 36%. Enhanced sensitivity to radial transport is confirmed by comparing phase images from flake 1 and flake 2 at the same frequency in FIG. 19. Although the signal-to-noise ratio is lower for flake 2 (due to the lower coefficient of thermoreflectance of Ti compared to Au at 532 nm), the increased sensitivity significantly reduced uncertainty in determining κ of encased single-layer graphene.

Figures 20A, 20B, 20C:
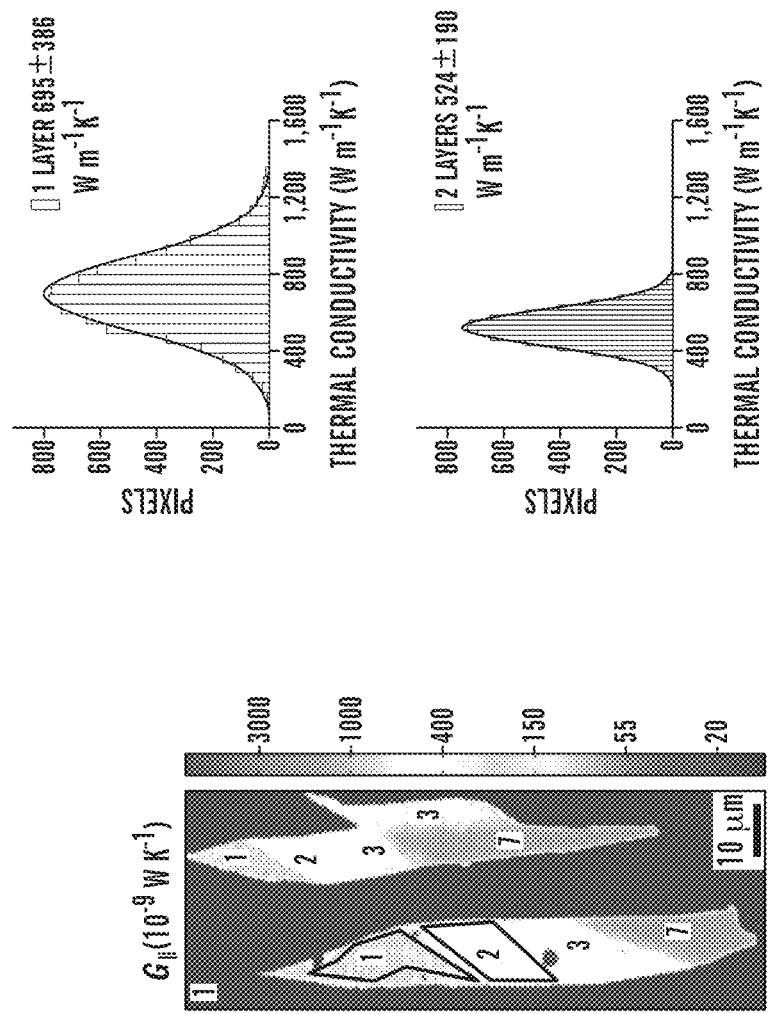

The thermal conductance maps for the two samples are shown in FIG. 20. The in-plane thermal conductance values for each layer were converted to thermal conductivities using κ=G/nt, where n is the number of layers and t=0.35 nm is the thickness of monolayer graphene.[21] Pixel statistics was used to calculate error bars, selecting regions with constant layer thickness and fitting the resulting histograms with normal distributions. This accounts for sources of statistical noise in the measurement.

To account for additional uncertainty introduced by the values of physical properties in the thermal model, the property maps were fitted three times using the upper bound, average, and lower bound of the metal layer thermal conductivity, which was by far the largest factor affecting the fitted values.

Figure 21A:
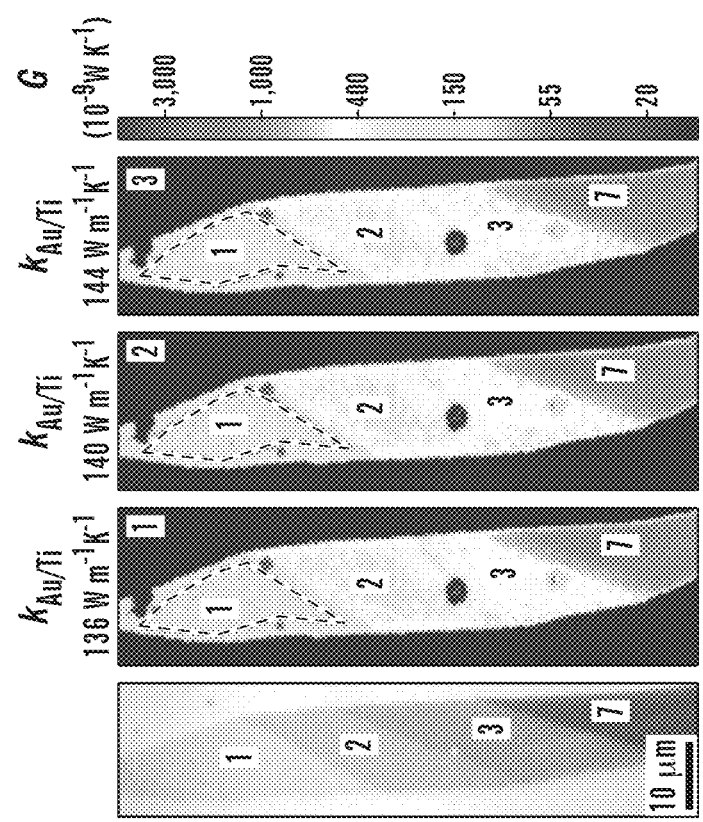
FIG. 21A is a set of in-plane thermal conductance $G_\parallel$ maps of flake 1 fitted with three j values of Au/Ti. The images are labeled from left to right as 1, 2, and 3.
Figure 21B:
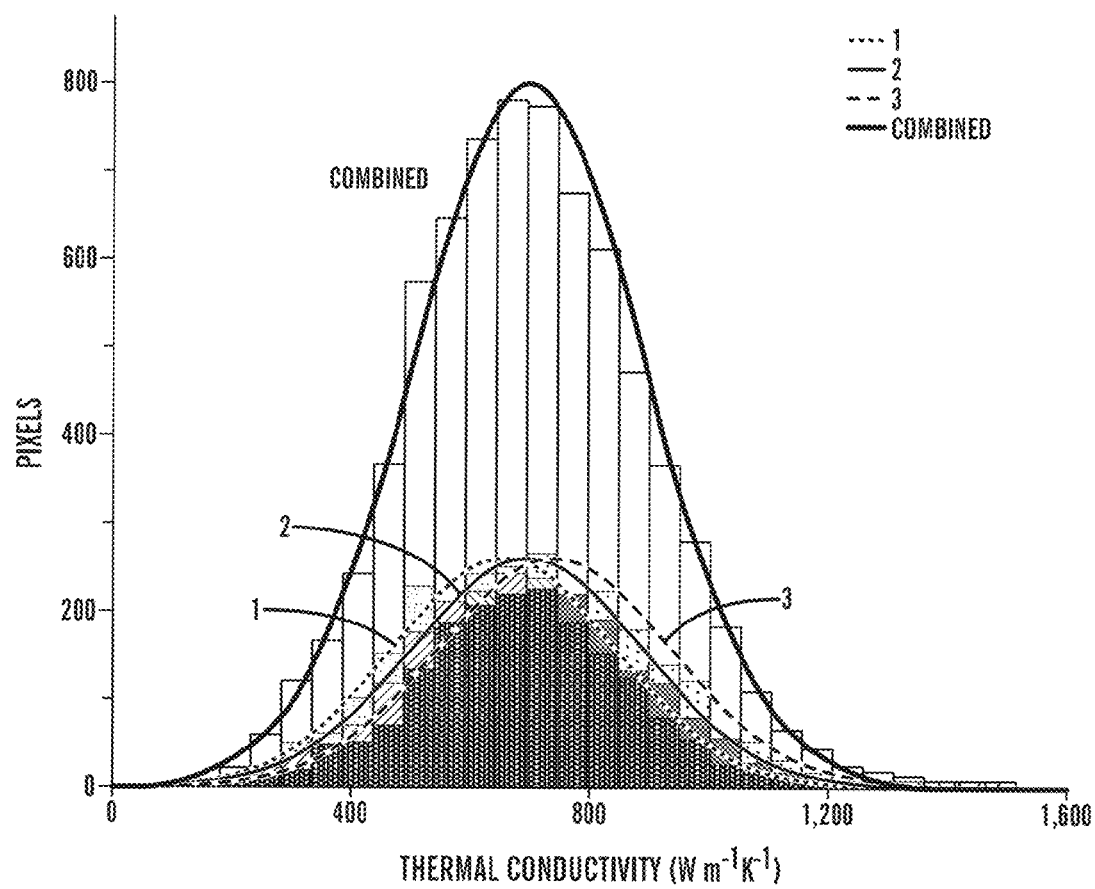
FIG. 21B is a plot of the thermal conductivity data histograms converted from the conductance pixel data in the labeled polygons of FIG. 21A. The grey histogram is the total data distribution by combining all three histograms together. The colored lines are fits to the normal distribution.

In addition, it was found that fitting effective spot sizes with the thermal model on the well calibrated silicon reference sample reduces the uncertainty in graphene values. Three sets of effective pump and probe spot radii for the 50× objective were first fitted with the thermal model on the silicon reference sample, using 136 W m$^{-1}$ K$^{-1}$, 140 W m$^{-1}$ K$^{-1}$, and 144 W m$^{-1}$ K$^{-1}$ as the thermal conductivity of the Au/Ti layer. FIG. 21A shows the fitted in-plane thermal conductance maps corresponding to the three sets of j and spot sizes. The pixel data from the selected regions, such as the single layer labeled by the dashed boxes in FIG. 21A, were converted to thermal conductivity values by dividing with the thickness of monolayer graphene. The three thermal conductivity data histograms, shown in FIG. 21B, are very close to each other, indicating that statistical noise dominates the uncertainty. The three histograms were then combined in FIG. 21B to get the total distribution. The average is defined as the measured value and twice the standard deviation is defined as the uncertainty. All the data analyses for flake 1 and flake 2 including the oxide regions without graphene were performed based on this procedure. The resulting values for the TBC and thermal conductivity of the two flakes are summarized in FIG. 22.

Figure 22A:
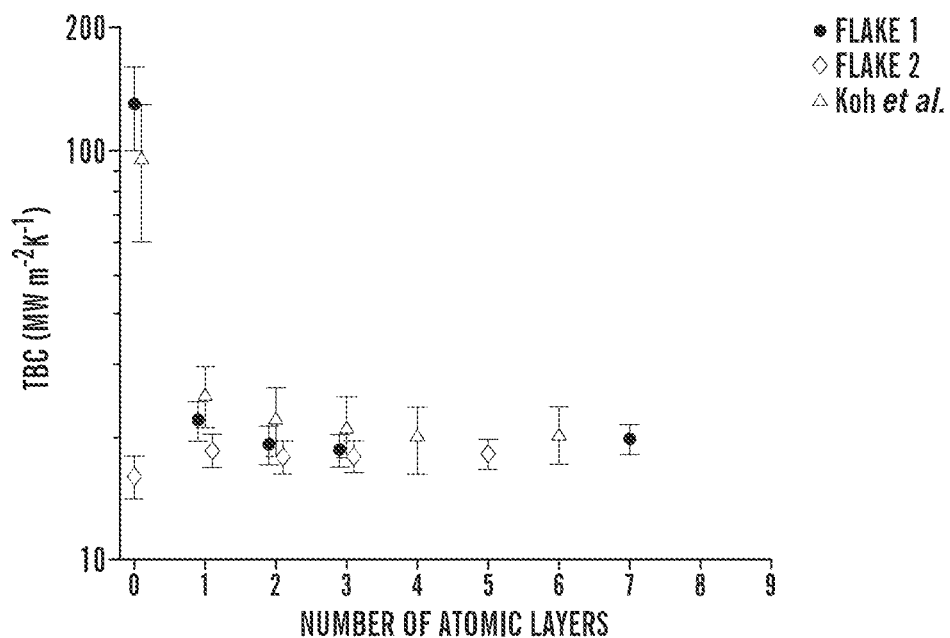
FIG. 22A is a plot of TBC for the measured samples and literature values for TBC of Au/Ti/graphene/$SiO_2$ (up triangles).

Considering first the TBC values in FIG. 22A, for flake 1, the presence of graphene significantly reduces the TBC compared to that of the metal/SiO$_2$ interface of the surrounding substrate (zero layers). For flake 2, the zero-layer TBC is almost an order of magnitude lower than that for flake 1. This is likely due to the contaminating nanoparticles shown in FIG. 14B, since a surface roughened by nanoparticles has been shown to reduce the TBC between a metal and a substrate.[23] In this case, the graphene improved cross-plane heat transfer. While not wishing to be bound by theory, a possible explanation for the enhancement is that graphene conformed to the contours of the contaminated surface,[24,25] increasing the thermal coupling between Ti and SiO$_2$.

From TDTR measurements from 50 to 500 K, Koh et al. found that heat flow across the graphene interface is governed by the Kapitza thermal resistances of the metal/graphene and graphene/SiO$_2$ interfaces acting in series: $G_{total}^{-1} = G_{metal/graphene}^{-1} + G_{graphene/SiO_2}^{-1}$.[10] By approximating $G_{metal/graphene}$ with $G_{metal/graphite}$=46 MW m$^{-2}$ K$^{-1}$, which with FDTR was measured for Ti deposited on the natural graphite source, G of the single-layer graphene/SiO$_2$ interface was estimate to be 42 MW m$^{-2}$ K$^{-1}$ and 31 MW m$^{-2}$ K$^{-1}$ for flake 1 and flake 2, respectively, comparable to values reported in Refs. 26 and 27. For the two samples, TBC of the single-layer graphene/SiO$_2$ interface is higher than that of few-layer graphene/SiO$_2$ interfaces, i.e., 30% higher for flake 1 and 7% higher for flake 3. Prasher has shown theoretically that the TBC of a van der Waals (vdW) contact depends positively on the adhesion energy of the interface,[28] implying that the adhesion energy between single-layer graphene and SiO$_2$ is larger than that between few-layer graphene and SiO$_2$, consistent with the measurement in Ref 25 that adhesion energy between multilayer graphene and SiO$_2$ drops from 0.45 J m$^{-2}$ to 0.31 J m$^{-2}$ when the layer number increases from one to two or more.

Figure 22B:
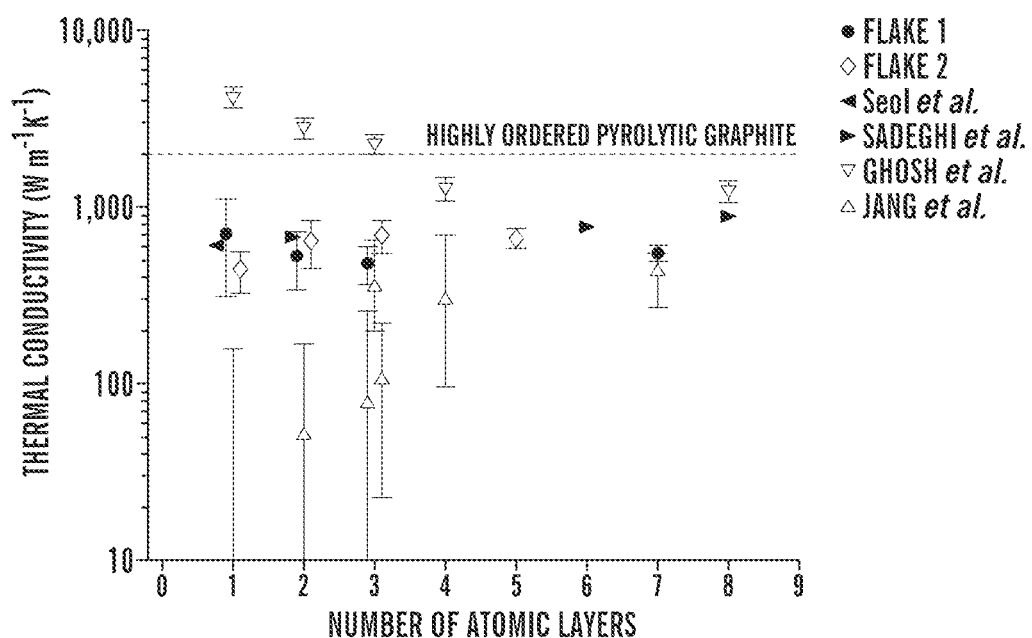
FIG. 22B is a plot of K of the two samples as a function of the number of atomic layers. The layer coordinates have been offset slightly for clarity. For comparison, literature values are also shown for highly ordered pyrolytic graphite (dashed line), suspended single-layer and few-layer graphene (inverted triangles), single-layer graphene supported on $SiO_2$ (left triangles), few-layer graphene supported on $SiO_2$ (right triangles), and single-and few-layer graphene encased between two $SiO_2$ layers (up triangles). Error bars indicate 95% confidence based on three pixel histograms.

Turning to the in-plane results in FIG. 22B, the obtained values are similar to those reported for single- and few-layer graphene supported on SiO$_2$ (Refs. 8 and 11) and higher than values reported for single- and few-layer graphene encased by two layers of SiO$_2$,[9] suggesting that depositing Ti on graphene that had already conformed to the SiO$_2$ substrate[24,25] has no significant impact on the basal-plane thermal conductivity.

The phonon MFPs in single-layer graphene and few-layer graphene for the graphene samples were estimated using the 2D kinetic theory: $\kappa = (1/2)Cv\Lambda$, where $\kappa$ is the thermal conductivity, C is the volumetric heat capacity, v is the averaged phonon velocity, $\Lambda$ is the phonon MFP, and the factor $1/2$ is due to the 2D nature of graphene.[15] This simplified expression is based on the gray approximation that all phonons have the same group velocity and lifetime. Because the transverse acoustic (TA) and longitudinal acoustic (LA) phonon modes in graphene have linear dispersions near the zone center[29] and the measurement temperature is well below graphite's Debye temperature (~2000 K in-plane[30]), this simple kinetic theory is suitable for estimating the phonon MFPs in graphene. C=1.57×10$^6$ J m$^{-3}$ K$^{-1}$ at 300 K was used from the volumetric heat capacity of graphite.[18] v is an average of LA and TA phonon velocities in graphene using $$\frac{1}{v^2} = \frac{1}{2}\left(\frac{1}{v_{LA}^2} + \frac{1}{v_{TA}^2}\right),$$

[31] where $v_{LA}$=21.3 km s$^{-1}$ and $v_{TA}$=13.6 km s$^{-1}$ were taken from Ref. 29. Using these literature values and the measured K values, the room temperature $\Lambda$ was derived and the results were summarized in Table II.

TABLE II

Estimated room temperature phonon MFPs in the graphene samples.

| | Phonon MFPs | |
|---|---|---|
| Sample | Single-layer (nm) | Few-layer (nm) |
| Flake 1 | 55 | 42 |
| Flake 2 | 34 | 51 |

A method for imaging sub-surface graphene in multilayer systems is described, and quantitative maps of both in-plane and cross-plane thermal conductance for single-layer graphene and few-layer graphene encased between a metal and SiO$_2$ are presented, yielding definite values for $\kappa$ of encased single-layer graphene. It was found that graphene decreased the TBC between Ti and SiO$_2$ for clean interfaces, but enhanced the conductance for a contaminated interface. Comparison with reported K for graphene supported on SiO$_2$ suggests a minimal impact from the deposited Ti on the thermal conductivity of graphene encased by Ti and SiO$_2$.

References for Example 2

1. S. Z. Butler, et al., "Progress, challenges, and opportunities in two-dimensional materials beyond graphene," ACS Nano 7, 2898 (2013).
2. K. S. Novoselov, et al., "Electric field effect in atomically thin carbon films," Science 306, 666 (2004).
3. A. A. Balandin, "Thermal properties of graphene and nanostructured carbon materials," Nature Mater. 10, 569 (2011).

4. D. L. Nika, et al., "Lattice thermal conductivity of graphene flakes: Comparison with bulk graphite," Appl. Phys. Lett. 94, 203103 (2009).
5. D. L. Nika, et al., "Theoretical description of thermal transport in graphene: The issues of phonon cut-off frequencies and polarization branches," Phys. Status Solidi B 248, 2609 (2011).
6. M. H. Bae, et al., "Scaling of high-field transport and localized heating in graphene transistors," ACS Nano 5, 7936 (2011).
7. E. Pop, et al., "Thermal properties of graphene: Fundamentals and applications," MRS Bull. 37, 1273 (2012).
8. J. H. Seol, et al., "Two-dimensional phonon transport in supported graphene," Science 328, 213-216 (2010).
9. W. Jang, et al., "Thickness-dependent thermal conductivity of encased graphene and ultrathin graphite," Nano Lett. 2010, 3909.
10. Y. K. Koh, et al., "Heat conduction across monolayer and few-layer graphenes," Nano Lett. 10, 4363 (2010).
11. M. M. Sadeghi, et al., "Phonon-interface scattering in multi-layer graphene on an amorphous support," Proc. Natl. Acad. Sci. U.S.A. 110, 16321 (2013).
12. K. L. Grosse, et al., "Nanoscale Joule heating, Peltier cooling and current crowding at graphene-metal contacts," Nat. Nanotechnol. 6, 287 (2011).
13. J. Yang, et al., "Thermal property microscopy with frequency domain thermoreflectance," Rev. Sci. Instrum. 84, 104904 (2013).
14. A. J. Schmidt, et al., "A frequency-domain thermoreflectance method for the characterization of thermal properties," Rev. Sci. Instrum. 80, 094901 (2009).
15. S. Ghosh, et al., "Extremely high thermal conductivity of graphene: Prospects for thermal management applications in nanoelectronic circuits," Appl. Phys. Lett. 92, 151911 (2008).
16. X. Wang, et al., "Thermal annealing of exfoliated graphene," J. Nanomater. 2013, 1.
17. B. C. Gundrum, et al., "Thermal conductance of metal-metal interfaces," Phys. Rev. B 72, 245426 (2005).
18. D. R. Lide, CRC Handbook of Chemistry and Physics, edited by D. R. Lide (Taylor & Francis, Boca Raton, Fla., 2007).
19. N. W. Ashcroft and D. N. Mermin, Solid State Physics (Harcourt College, New York, 1976).
20. H. C. Chien, et al., "Thermal conductivity measurement and interface thermal resistance estimation using SiO2 thin film," Rev. Sci. Instrum. 79, 054902 (2008).
21. A. Gupta, et al., "Raman scattering from high-frequency phonons in supported n-graphene layer films," Nano Lett. 6, 2667 (2006).
22. S. Ghosh, et al., "Dimensional crossover of thermal transport in few-layer graphene," Nature Mater. 9, 555 (2010).
23. P. E. Hopkins, et al., "Controlling thermal conductance through quantum dot roughening at interfaces," Phys. Rev. B 84, 035438 (2011).
24. W. G. Cullen, et al., "High-fidelity conformation of graphene to SiO2 topographic features," Phys. Rev. Lett. 105, 215504 (2010).
25. S. P. Koenig, et al., "Ultrastrong adhesion of graphene membranes," Nat. Nanotechnol. 6, 543 (2011).
26. Z. Chen, et al., "Thermal contact resistance between graphene and silicon dioxide," Appl. Phys. Lett. 95, 161910 (2009).
27. K. F. Mak, et al., "Measurement of the thermal conductance of the graphene/SiO2 interface," Appl. Phys. Lett. 97, 221904 (2010).
28. R. Prasher, "Acoustic mismatch model for thermal contact resistance of van der Waals contacts," Appl. Phys. Lett. 94, 041905 (2009).
29. D. Nika, et al., "Phonon thermal conduction in graphene: Role of Umklapp and edge roughness scattering," Phys. Rev. B. 79, 155413 (2009).
30. T. Tohei, et al., "Debye temperature and stiffness of carbon and boron nitrade polymorphs from first principles calculations," Phys. Rev. B. 73, 064304 (2006).
31. C. Dames and G. Chen, "Theoretical phonon thermal conductivity of Si/Ge superlattice nanowires," J. Appl. Phys. 95, 682 (2004).

What is claimed is:

1. A method of performing a frequency domain thermoreflectance measurement, the method comprising:
   (i) projecting a first beam of radiation onto a sample while a heat source is applied to the sample, wherein the heat source is modulated at a modulation frequency;
   (ii) measuring reflected radiation from the first beam of radiation at at least two modulation frequencies simultaneously, wherein amplitude and/or phase data of the reflected radiation are obtained, and wherein the modulation frequencies are determined from sensitivity of amplitude and/or phase of the reflected radiation to a given thermophysical property;
   (iii) repeating steps (i) and (ii) at a plurality of spots in the sample; and
   (iv) producing a two-dimensional (2D) image of at least one thermophysical property of the sample based on the measurements.

2. The method of claim 1, wherein the measurement is at six modulation frequencies simultaneously.

3. The method of claim 1, wherein one modulation frequency is at or near maximum sensitivity to the given thermophysical property.

4. The method of claim 1, wherein the modulation frequencies are spaced to fit a desired set of thermophysical properties using a sensitivity function.

5. The method of claim 1, wherein the modulation frequencies are in the range of 1 kHz to 50 MHz.

6. The method of claim 1, wherein the measurement is done using a lock-in amplifier.

7. The method of claim 1, further comprising moving the sample relative to the first beam of radiation, thereby scanning the first beam of radiation across the sample.

8. The method of claim 1, wherein the thermophysical property is determined through fitting of data obtained from the measurement.

9. The method of claim 1, wherein the thermophysical property is selected from the group consisting of film thickness, density, heat capacity, thermal conductivity, in-plane thermal conductivity, cross-plane thermal conductivity, and thermal interface conductance.

10. The method of claim 1, wherein the 2D image exhibits a maximum spatial resolution of about 200 nm.

11. The method of claim 1, wherein the first beam of radiation is a laser beam.

12. The method of claim 1, comprising producing a 2D image of two or more thermophysical properties of the sample.

13. The method of claim 12, wherein the two or more thermophysical properties are in-plane thermal conductivity and cross-plane thermal conductivity.

14. The method of claim 1, wherein the sample is a bulk sample or a multilayered sample.

15. The method of claim 14, wherein the sample is coated with a layer of metal.

16. The method of claim 1, wherein the heat source is produced by a second beam of radiation projected onto the sample.

17. The method of claim 3, wherein the second beam of radiation is aligned coaxially with the first beam of radiation.

18. The method of claim 16, wherein the second beam of radiation is modulated via a sine wave for each modulation frequency.

19. The method of claim 16, wherein the second beam of radiation is a laser beam.

20. A method of performing a frequency domain thermoreflectance measurement, the method comprising:
   (i) projecting a first beam of radiation onto a sample while a heat source is applied to the sample, wherein the heat source is modulated at a modulation frequency;
   (ii) measuring reflected radiation from the first beam of radiation at at least two modulation frequencies simultaneously, wherein amplitude and/or phase data of the reflected radiation are obtained, and wherein the modulation frequencies are spaced to fit a desired set of thermophysical properties using a sensitivity function;
   (iii) repeating steps (i) and (ii) at a plurality of spots in the sample; and
   (iv) producing a two-dimentional (2D) image of at least one thermophysical property of the sample based on the measurements.

* * * * *

UNITED STATES PATENT AND TRADEMARK OFFICE
CERTIFICATE OF CORRECTION

PATENT NO. : 9,927,350 B2  
APPLICATION NO. : 14/511903  
DATED : March 27, 2018  
INVENTOR(S) : Schmidt et al.

Page 1 of 1

It is certified that error appears in the above-identified patent and that said Letters Patent is hereby corrected as shown below:

On the Title Page

Item (12), replace "Schmidt" with --Schmidt et al.--; and

Item (72), add Inventor: --Jia Yang, Franklin, MA (US)--.

Signed and Sealed this
Twenty-eighth Day of February, 2023

Katherine Kelly Vidal
*Director of the United States Patent and Trademark Office*